US012562285B2

(12) United States Patent
Montano et al.

(10) Patent No.: US 12,562,285 B2
(45) Date of Patent: Feb. 24, 2026

(54) METHODS AND SYSTEMS FOR SEMANTICS BASED GENERATION OF CONNECTIONS BETWEEN SEPARATE DATA SETS

(71) Applicant: ID Business Solutions, Ltd., Woking (GB)

(72) Inventors: Alberto Pascual Montano, Paracuellos de Jarama (ES); Shun Mao, Katy, TX (US); Scott Weiss, Loveland, CO (US)

(73) Assignee: ID BUSINESS SOLUTIONS, LTD., Woking (GB)

( * ) Notice: Subject to any disclaimer, the term of this patent is extended or adjusted under 35 U.S.C. 154(b) by 0 days.

(21) Appl. No.: 18/833,639

(22) PCT Filed: Jan. 27, 2023

(86) PCT No.: PCT/IB2023/000045
§ 371 (c)(1),
(2) Date: Jul. 26, 2024

(87) PCT Pub. No.: WO2023/144629
PCT Pub. Date: Aug. 3, 2023

(65) Prior Publication Data
US 2025/0149186 A1     May 8, 2025

Related U.S. Application Data

(60) Provisional application No. 63/303,704, filed on Jan. 27, 2022.

(51) Int. Cl.
*G16H 50/70* (2018.01)
*G06F 16/28* (2019.01)

(52) U.S. Cl.
CPC ........... *G16H 50/70* (2018.01); *G06F 16/287* (2019.01)

(58) Field of Classification Search
None
See application file for complete search history.

(56) References Cited

U.S. PATENT DOCUMENTS 10,685,407 B1 *  6/2020  Cabrera ............... G06Q 40/123
2003/0198930 A1 *  10/2003  Stuppy .................... G09B 7/00
434/322

(Continued)

OTHER PUBLICATIONS

International Search Report and Written Opinion issued for PCT/IB2023/000045, mailed Jun. 13, 2023, 69 pgs.

(Continued)

*Primary Examiner* — Thu N Nguyen
(74) *Attorney, Agent, or Firm* — PATENT LAW WORKS LLP

(57) ABSTRACT

A method and system for identifying connections between data items in an updatable data repository includes dynamically receiving a plurality of data items, each data item including one or more controlled terms, displaying the dynamically received data items on a display, and identifying one or more connections between data items from different updatable sources based on the display. A method and system for identifying connections between data items in an updatable data repository also includes dynamically receiving a plurality of data items, each data item including one or more controlled terms, defining degrees of similarity between the data items, ranking the data items with respect to one another based on the degree of similarity therebetween, and identifying one or more connections between data items from different updatable sources based on the ranking. The data items are also updated contemporaneously when the sources thereof are updated.

25 Claims, 14 Drawing Sheets

Although it is becoming evident that an individual's immune system has a decisive influence on disease progression, pathogenesis is largely unknown. In this study, we aimed to profile the host transcriptome of COVID patients from nasopharyngeal samples along with virus genomic features isolated from respective host, and a comparative analyses of differential host responses in various infection systems.

Unique and rare missense mutations in 3C-like protease observed in all of our reported isolates. Functional enrichment analysis exhibited that the host induced responses are mediated by innate immunity, interferon, and cytokine stimulation. Surprisingly, induction of apoptosis, phagosome, antigen presentation, hypoxia response was lacking within these patients. Upregulation of immune and cytokine signaling genes such as CCL4, TNFA, IL6, IL1A, CCL3, CXCL2, IFN, and CCR1 were observed in lungs. Lungs lacked the overexpression of angiotensin converting enzyme as suspected, however, high ACE2 but low DPP4 expression was observed in nasopharyngeal cells.

Keywords: COVID-19; Genome variations; Host transcriptional response; Immune response; Integrins; SARS_COV-2.

Synonyms: COVID-19, SARS_COV-2
Tagged as DISEASE: COV19

(56) References Cited

U.S. PATENT DOCUMENTS

| 2004/0015514 | A1* | 1/2004 | Melton | ............... | G06F 16/2228 |
| 2018/0173699 | A1* | 6/2018 | Tacchi | ................. | G06F 16/358 |
| 2019/0005395 | A1* | 1/2019 | Dutkowski | ............ | G06N 5/022 |

OTHER PUBLICATIONS

International Preliminary Report on Patentability, issued for PCT/IB2023/000045, mailed Aug. 8, 2024, 10 pgs.
Communication pursuant to Rules 161(1), 162 EPC, issued from the European Patent Office on Sep. 5, 2024, 3 pgs.

* cited by examiner

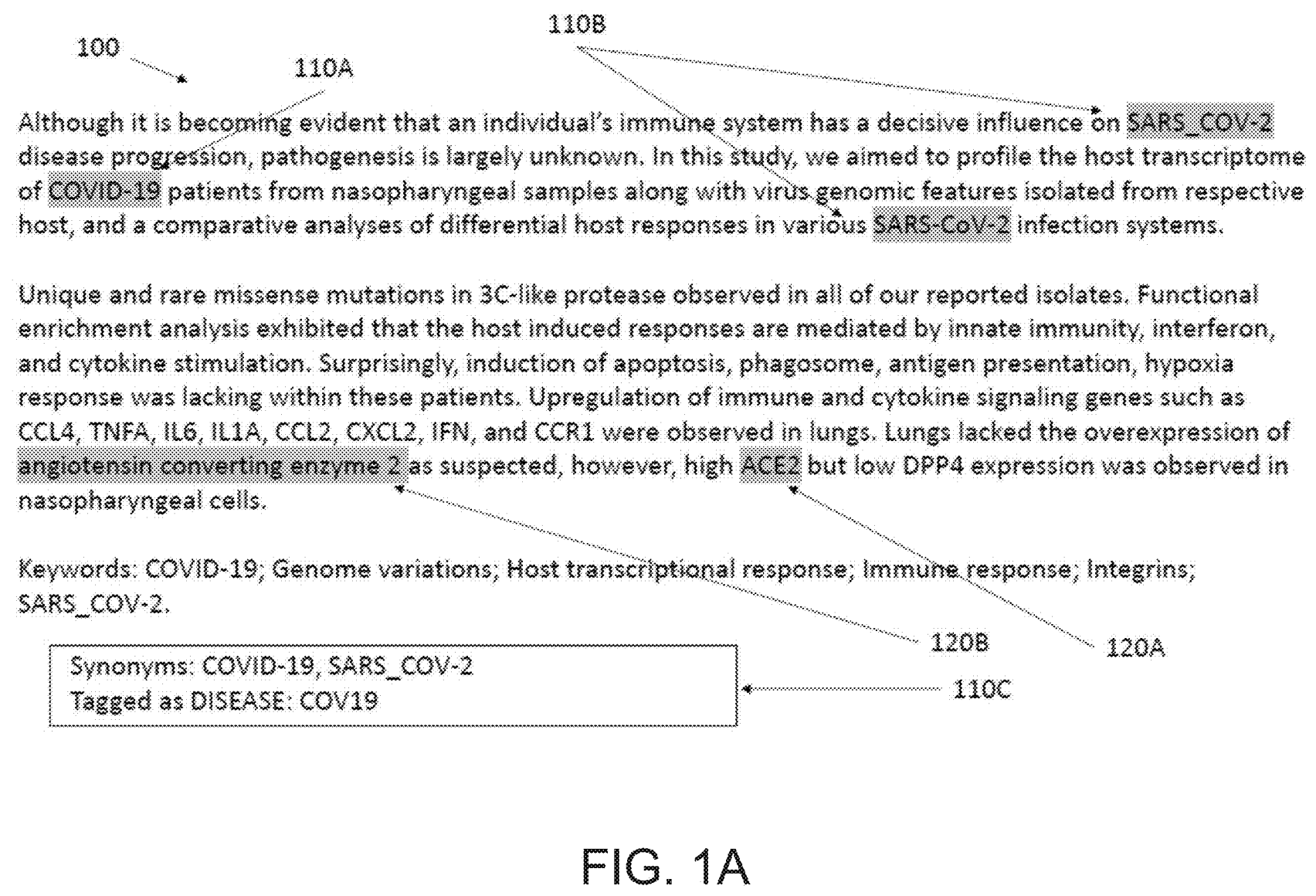

100

110A

110B

Although it is becoming evident that an individual's immune system has a decisive influence on SARS_COV-2 disease progression, pathogenesis is largely unknown. In this study, we aimed to profile the host transcriptome of COVID-19 patients from nasopharyngeal samples along with virus genomic features isolated from respective host, and a comparative analyses of differential host responses in various SARS-CoV-2 infection systems.

Unique and rare missense mutations in 3C-like protease observed in all of our reported isolates. Functional enrichment analysis exhibited that the host induced responses are mediated by innate immunity, interferon, and cytokine stimulation. Surprisingly, induction of apoptosis, phagosome, antigen presentation, hypoxia response was lacking within these patients. Upregulation of immune and cytokine signaling genes such as CCL4, TNFA, IL6, IL1A, CCL2, CXCL2, IFN, and CCR1 were observed in lungs. Lungs lacked the overexpression of angiotensin converting enzyme 2 as suspected, however, high ACE2 but low DPP4 expression was observed in nasopharyngeal cells.

120A

120B

110C

Keywords: COVID-19; Genome variations; Host transcriptional response; Immune response; Integrins; SARS_COV-2.

Synonyms: COVID-19, SARS_COV-2
Tagged as DISEASE: COV19

FIG. 1A

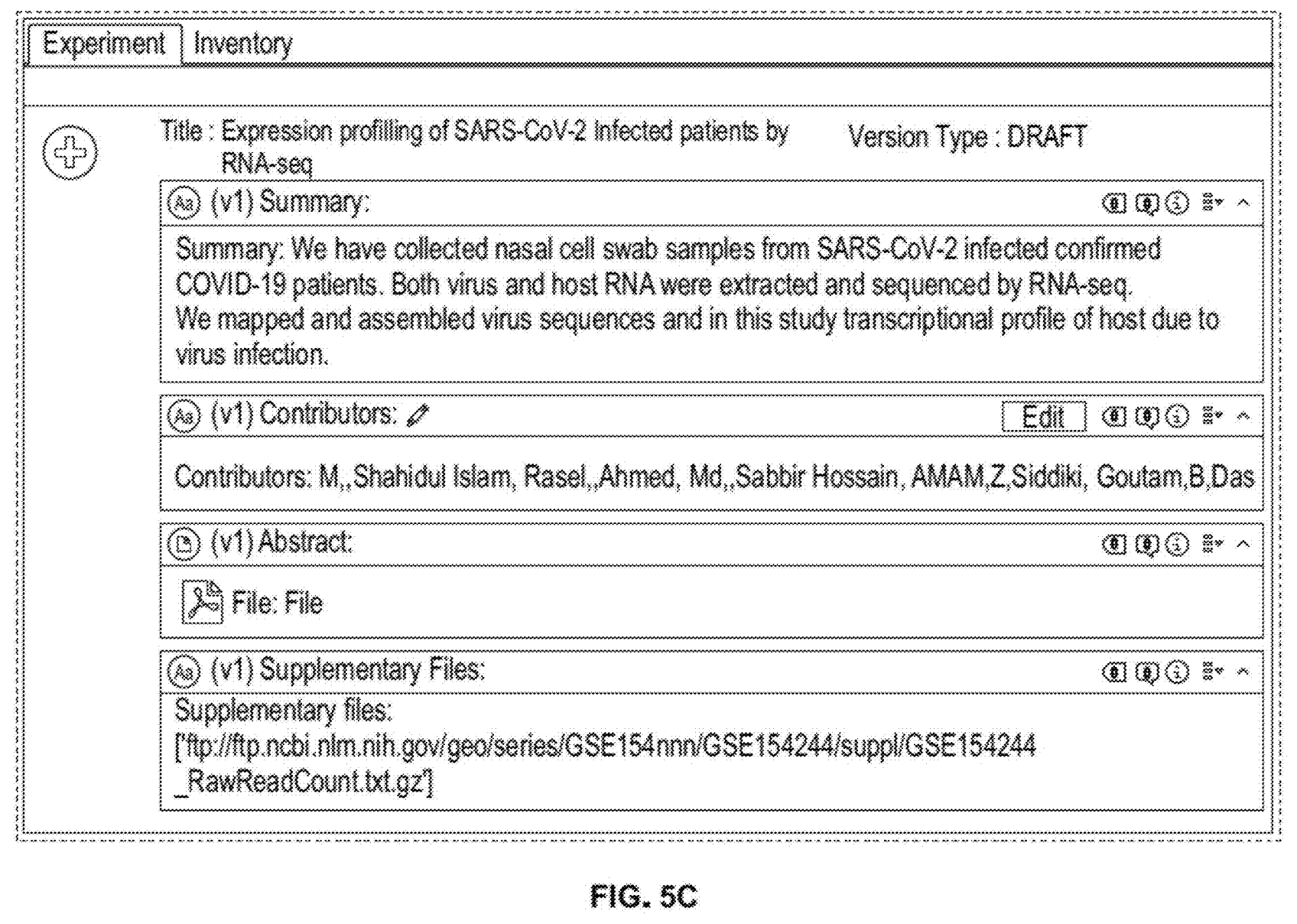

Experiment | Inventory

Title : Expression profiling of SARS-CoV-2 infected patients by     Version Type : DRAFT
RNA-seq (Aa) (v1) Summary:

Summary: We have collected nasal cell swab samples from SARS-CoV-2 infected confirmed
COVID-19 patients. Both virus and host RNA were extracted and sequenced by RNA-seq.
We mapped and assembled virus sequences and in this study transcriptional profile of host due to
virus infection.

(Aa) (v1) Contributors: ✏

Contributors: M.,Shahidul Islam, Rasel,Ahmed, Md.,Sabbir Hossain, AMAM,Z,Siddiki, Goutam,B,Das       Edit (b) (v1) Abstract:

📄 File: File (Aa) (v1) Supplementary Files:

Supplementary files:
[ftp://ftp.ncbi.nlm.nih.gov/geo/series/GSE154nnn/GSE154244/suppl/GSE154244
_RawReadCount.txt.gz]

FIG. 5C

METHODS AND SYSTEMS FOR SEMANTICS BASED GENERATION OF CONNECTIONS BETWEEN SEPARATE DATA SETS

CROSS-REFERENCE TO RELATED APPLICATIONS

The present application is a national phase entry under 35 U.S.C. § 371 of International Patent Application No. PCT/IB2003/000045, filed Jan. 27, 2023, designating the United States of America, and published in English as International Patent Publication No. WO 2023/144629 on Aug. 3, 2023, which claims the benefit under Article 8 of the Patent Cooperation Treaty to U.S. Provisional Patent Application No. 63/303,704 filed Jan. 27, 2022; all of which are incorporated by reference herein.

BACKGROUND

When attempting to exploit large amounts of data such as, e.g., large experimental data sets from a number of scientific teams researching various subjects, some of the data generated by these research teams may be lost because it is not indexed or referenced so as to render it searchable. In particular, laboratory notebooks or electronic workbooks may include large amounts of data, experimental protocols and results, and the like, that are never reviewed and made accessible. In addition, even when the data is digitally recorded in a searchable format, the data to be searched must be known in advance in order to be entered in a search tool. Data that is present in a large data repository but concealed therein due to the size of the data repository, may not be able to be found via a typical search tool that relies on, e.g., a keyword or Boolean search.

SUMMARY

In one aspect, the technology relates to a method and system for identifying connections between data items in an updatable data repository, the method including dynamically receiving a plurality of data items from the updatable data repository, the data items being provided by a plurality of updatable sources, each data item including one or more controlled terms, displaying the dynamically received data items on a display, and identifying one or more connections between data items from different updatable sources based on the display, the dynamically received data items being updated contemporaneously when the sources thereof are updated.

In an example of the above aspect, for each data item, each controlled term defines one or more characteristics of the data item. In another example, characteristics comprise at least one of a drug, an experiment, a gene, a device, a chemical molecule, a research center, a research team, a location, and an event. In an example, the data items only include controlled terms. In yet another example, the displayed data items are separated by distances related to a degree of similarity therebetween, and identifying the one or more connections is based on the distances. In another example, the degree of similarity between two data items is defined by at least one of a number and a frequency of controlled terms shared by the two data items.

In yet another example of the above aspect, the method further includes defining a distance threshold, wherein identifying the one or more connections comprises identifying data items that are separated by a distance that is less than the distance threshold. In another example, the data items are grouped in one or more clusters on the display, the data items in each cluster sharing same controlled terms. In an example, the updatable data repository includes electronic workbooks, also referred to as laboratory electronic notebooks. In yet another example, when the dynamically received data is updated, at least one connection is identified as a result thereof.

In another aspect, the technology relates to a data connection finder that includes a data receiver, an updatable data repository functionally coupled to the data receiver, a processor operatively coupled to the data receiver, to the updatable data repository and to the display device, and a memory coupled to the processor, the memory storing instructions. The instructions, when executed by the processor, perform a set of operations including dynamically receiving, at the data receiver, a plurality of data items from the updatable data repository, the data items being provided by a plurality of updatable sources, each data item including one or more controlled terms, displaying the dynamically received data items on a display of the display device, and identifying, via the processor, one or more connections between data items from different updatable sources based on the display, the dynamically received data items being updated contemporaneously when the sources thereof are updated.

In an example of the above aspect, the displayed data items are separated, on the display of the display device, by distances related to a degree of similarity therebetween, and identifying the one or more connections is based on the distances. In another example, degree of similarity between two data items is defined by at least one of a number and a frequency of controlled terms shared by the two data items. In yet another example, the set of operations further include defining a distance threshold, wherein identifying the one or more connections comprises identifying data items that are separated by a distance that is less than the distance threshold. In another example, when the dynamically received data is updated, at least one connection is identified as a result thereof via the processor.

In another aspect, the technology relates to a method for identifying connections between data items in an updatable data repository, the method including dynamically receiving a plurality of data items from the updatable data repository, the data items being provided by a plurality of updatable sources, each data item including one or more controlled terms, defining degrees of similarity between the data items, ranking the data items with respect to one another based on the degree of similarity therebetween, and identifying one or more connections between data items from different updatable sources based on the ranking, wherein the data items are updated contemporaneously when the sources thereof are updated.

In an example of the above aspect, the degree of similarity between two data items is defined by at least one of a number and a frequency of controlled terms shared by the two data items. In another example, for each given data item, other data items are individually ranked based on the degree of similarity between the given data item and each of the other data items. In yet another example, any two data items share a same rank. In another example, the method further includes defining a rank threshold, wherein identifying the one or more connections comprises identifying data items that share a rank that is higher than the rank threshold. In yet another example, the method further includes providing the one or more identified connections.

BRIEF DESCRIPTION OF THE DRAWINGS

FIG. 1A is a schematic view of an example of data normalization to facilitate searching across disparate data sets having different or synonymous descriptions of a same data item by using controlled terms, in accordance with various aspects.

FIGS. 5A-5C are schematic diagrams illustrating tagged data items from different data sets, according to various aspects.

DETAILED DESCRIPTION

Figure 1B:
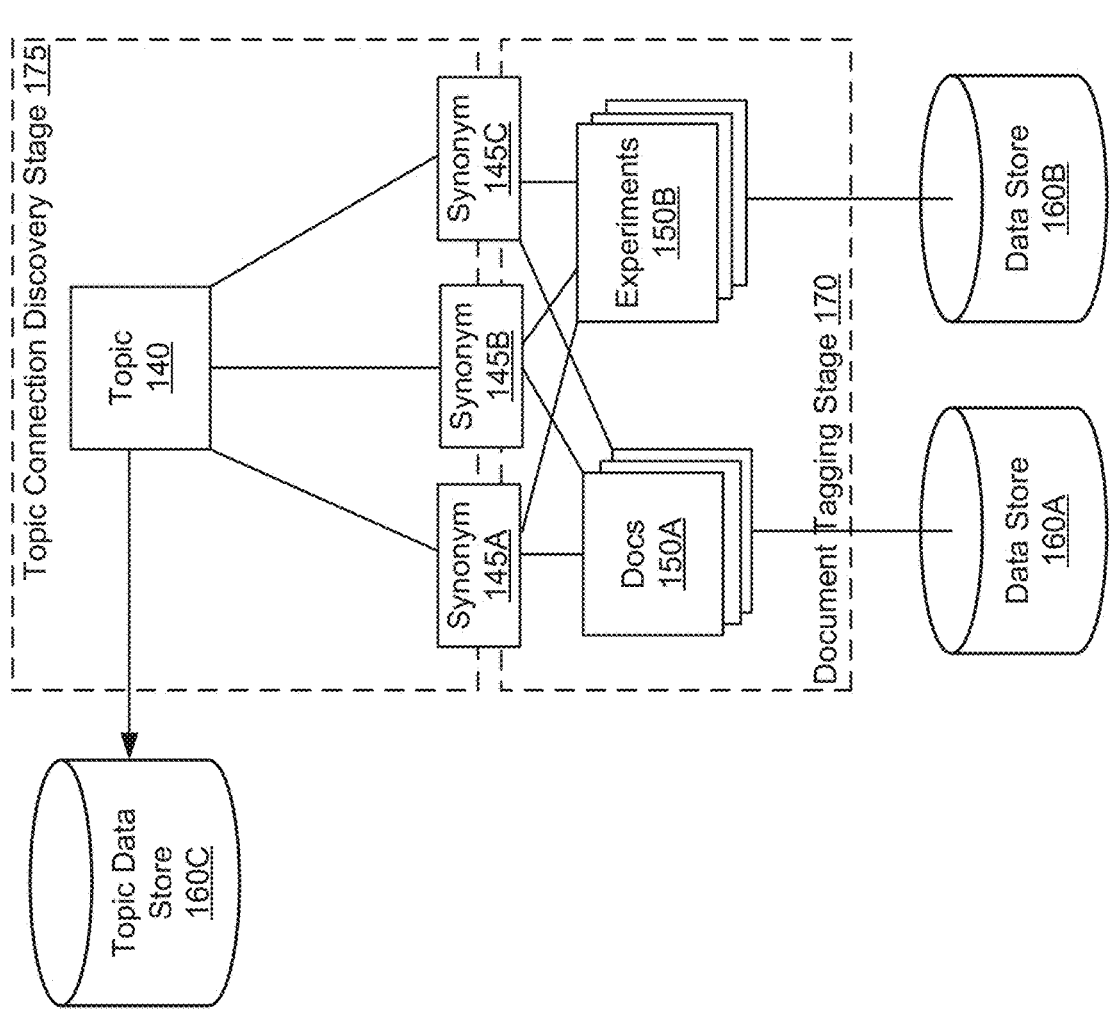
FIG. 1B is a high-level block diagram of an example process of data normalization, in accordance with various aspects.

There are large volumes of unstructured free text in various data repositories, such as, e.g., experimental data disseminated worldwide, as well as attached documents. These documents may include, e.g., laboratory notebooks or electronic workbooks, pictures, PDF documents, or documents in other commonly used formats other than a word processing format. These documents are typically difficult to search and/or find due to a number of factors including, e.g., the sheer amount of disseminated data. Such data often suffers from a lack of uniformity in the description thereof, typically because no single body owns the description of the various topics and concepts discussed therein.

For example, in the field of medical devices, terms describing or included in, e.g., drugs, genes, experimental reports, scientific publications, scientific protocols, technical standards, chemical molecules, research centers, research teams, locations, adverse events, antibody types, anatomy features, biochemicals, biotherapeutics, cell lines, cell types, company names, countries, medical devices, drug classes, clinical genetic variations, geographical locations, human phenotype, mechanisms of action, mutations, nucleic acid sequences, peptide sequences, clinical phase, protein types, regulatory agencies, research codes, species, and the like, are not always described in exactly the same manner, rendering searching and/or finding this data challenging. As a result, when searching for data that has been generated in a given scientific field, researchers are often dependent on the persons or entities that entered the data in, e.g., the laboratory notebooks or electronic workbooks, to access and analyze the data. Accordingly, these persons or entities in effect operate as gatekeepers of the information that is being sought. In other words, there is typically a lack of data democratization allowing various parties access to the data without gatekeepers creating a bottleneck to access the data. In this case, the gatekeepers may be, e.g., the persons or entities in charge of entering the data in the unstructured free text that is disseminated in publications and the like using a terminology that may not be shared by other persons or entities which also enter the data. As a result, the data flow between, e.g., various research teams, is slowed down, and so is the ability of researchers to access it and utilize it to make appropriate and useful findings.

There are several limitations in finding data in large data sets. Such limitations may include, e.g., findability, where data cannot be found by users through keyword search or natural language processing because of the lack of uniformity in the terminology used to describe the data. Another limitation in dealing with large data sets may be interoperability, which hampers data analysis, and which may lead to missing insights when analyzing the data, also due to the lack of uniformity in the terminology. In addition, although typical searches are based on known unknowns, where the object of the search is already known in advance and entered in a search tool via, e.g., keyword, Boolean search or natural language processing, relationships that are latent or as yet unknown, cannot typically be uncovered via these searching methods.

Accordingly, there is a need to not only harmonize the terminology used when entering the data in various laboratory notebooks, electronic workbooks, publications, or other media, but also to annotate relevant data items so as to identify them as synonyms. For example, annotating the relevant terms may be performed by adding identifying ontologies tags in the metadata of the terms, or in a data repository. A given tag may include various terms and synonyms of the data item via, e.g., named entity recognition (NER) or other method. The tags may provide uniformity in describing and referring to the data items, as well as the possibility of finding the various data items that share a same tag. There is also a need in rendering data models dynamic by allowing the data to be searched using various terminologies, as long as the different terminologies share the same tags. As a result, latent or previously unknown relationships or connections between seemingly unconnected sets of data may be uncovered. In various aspects, a tag assigned to a data item may include, e.g., a gene, a drug, an experimentation protocol, names of authors or inventors, dates of experimentation or publication, locations of research teams, a chemical molecule, a research center, a research team, an adverse event and the like. The tag may also include a number of synonyms so that a search based on any one of the synonyms may generate the same data item.

Accordingly, there is a technical problem that arises out of the lack of data democratization, where existing data classification and search methodologies may not allow to uncover all the relevant data due to the use of various terminologies and synonyms for the same data. A solution to this technical problem may include assigning a tag to each data item, the tag including a number of terms identifying the data item, including synonyms of the data item. There is also a technical problem that arises out of the fact that typical searching methods rely on the knowledge of what is being sought prior to performing a search, or on known relationships between data items in various sets of data, but does not uncover latent or previously unknown relationships between various data sets. A solution to this technical problem may include ranking the data items with respect to each other in terms of degrees of similarity, or displaying the data items on a display at distances that depend on the number and frequency of terms shared between the data items, and determining new, latent or previously unknown relationships between the data items based on the rank or the distances that separate them.

For illustrative purposes, FIG. 1A is a schematic view of an example of data normalization to facilitate searching across disparate data sets having different or synonymous descriptions of same data items by using controlled terms and/or semantic terms, also referred to as tags, in accordance with various aspects. In FIG. 1A, the free form text 100 includes a description of a given experimental report such as, e.g., a scientific publication or protocol discussing various drugs, genes, diseases, treatments, and the like, may be described. In addition, various synonyms of a same data item may be used in different experimental descriptions or data sources. The data sources may be, for example, laboratory notebooks or electronic workbooks. For example, the disease description "COVID-19" 110A may be used interchangeably with the virus that causes COVID-19, "SARS-_COV-2" 110B. However, both descriptions "COVID-19" 110A and "SARS_COV-2" 110B have a same tag associated thereto, the tag being stored in the metadata of the free form text 100 or in a data repository. Accordingly, both terms "COVID-19" 110A and "SARS_COV-2" 110B refer to the same disease, and a tag may be generated to associate both terms.

In various aspects, because one data source may use the description "COVID-19" 110A while another data source may use the description "SARS_COV-2" 110B, absent a uniformization of these descriptions, a search for "SARS-_COV-2" 110B across a number of data sets would uncover the description "SARS_COV-2" 110B but may not uncover the description "COVID-19" 110A even though both terms relate to the same disease. In various aspects, the various descriptions of the same disease "COVID-19" 110A may correspond to the same ontology and may be tagged with the same tag, e.g., the tag "DISEASE: COV19," and the same tag may refer to the same disease regardless of the synonym used in any other reference or publication. For example, the ontology described at 110C shows that various synonyms for the disease COVID-19 are considered to be equivalent and are all tagged as "DISEASE: COV19." Accordingly, a tag is created, one that includes various descriptions of the COVID-19 disease under the controlled term and/or semantic term, also referred to as tag "DISEASE: COV19," and this tag may be stored either in the metadata of the document or in a separate data repository. As a result, it may become possible for researchers or users to search across large amounts of data generated by different sources and using different terminologies by using a controlled term and/or semantic term such as, e.g., "DISEASE: COV19," and such search will uncover all versions or synonyms of the disease such as "COVID-19" 110A or "SARS_COV-2" 110B. Alternatively, if a user or searcher searches for the term "SARS_COV-2" 110B, references that describe "COVID-19" 110A may also be returned to the searcher because both descriptions share a same controlled term and/or semantic term, in this case the tag "DISEASE: COV19."

Similarly, in various aspects, the gene name "ACE2" 120A is related to "angiotensin converting enzyme 2" 120B, the protein expressed by the ACE2 gene. As such, both descriptions may be assigned a same tag to render searching for this specific gene, and to allow a searcher who searches for "ACE2" to also receive "angiotensin converting enzyme 2" as a result of their search. As a result, searching various data sources, laboratory notebooks, electronic workbooks, references and the like may uncover more significant results because the use of disparate descriptions may be normalized, rendering the data sources more searchable. Accordingly, information that was siloed due to individualized and non-uniform terminology may now be de-siloed and available for search by a wider population of searchers.

FIG. 1B is a high-level block diagram of an example process of data normalization and topic extraction, in accordance with various aspects. Continuing the example from FIG. 1A, various data sources, laboratory notebooks, electronic workbooks, references and the like may be stored in data store 160A and data store 160B, for example. While two data stores 160 are illustrated in FIG. 1B for simplicity, any number of data stores be used in such a system 105. Through a document tagging stage 170, documents 150A and experiments 150B may be automatically tagged using various techniques, such as a third-party software solution. Synonyms of the same characteristic, such as a disease or a gene name, may surface as synonym 145A, synonym 145B, and synonym 145C. For example, synonyms of the disease may be found, such as "COVID-19" 110A or "SARS_COV-2" 110B as shown in FIG. 1A. While three synonyms are illustrated in FIG. 1B, any number of synonyms may be found through the document tagging stage 170.

In the topic connection discovery stage 175, a topic 140 may be discovered to be connected to the synonyms 145A, 145B, and 145C using an unsupervised machine learning model that discovers hidden features in the processed data without any prior information. Using factorization techniques, such as non-negative matrix factorization, topic modelling may be performed where the input is a term-document matrix (a table with the frequency of terms or words in each document or experiment) and linear algebra is used for topic modelling. Returning to the example of FIG. 1A, a controlled term, such as "DISEASE: COV19," may be used as the topic 140 that refers to the synonyms "COVID-19" 110A or "SARS_COV-2" 110B as shown in FIG. 1A. The topic 140 is then stored in the topic data store 160C. In this way, terms, documents, and topics are all related, enabling visualizations of relationships in multiple ways.

Figure 2A:
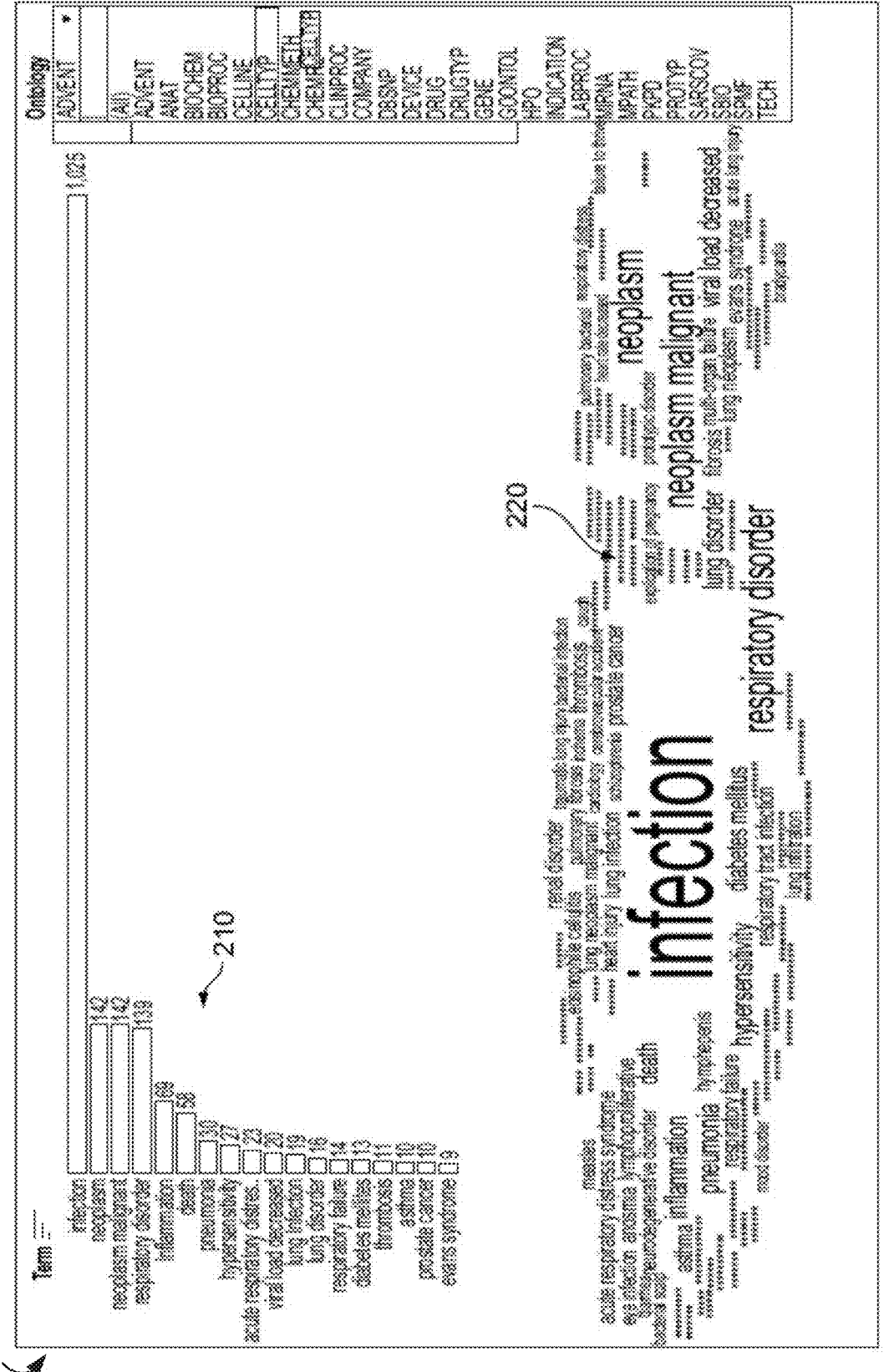
FIG. 2A is an illustration of a word distribution and a word density of controlled terms in a plurality of data sources, in accordance with various aspects.

FIG. 2A is a display 204 illustrating a word distribution histogram 210, and a word density illustration 220, of controlled terms and/or semantic terms in a plurality of data sources, in accordance with various aspects. In various aspects, when the controlled terms and/or semantic terms designating, e.g., drugs, genes, treatments, or the like, are gathered in free form from a variety of data sets or data sources, and are generated as discussed above with respect to FIG. 1A, the controlled terms and/or semantic terms may be displayed based on their frequency of occurrence within one or more data sources or data sets. The controlled terms and/or semantic terms that are assigned to the various terms are displayed based on their frequency of occurrence in display 210 in the form of a histogram. Accordingly, the histogram 210 provides a visual indication of the relative frequency of various controlled terms and/or semantic terms, and their relative importance within the realm of the available data sets or data sources. Similarly, the word density illustration 220 provides an illustration of the most frequently used controlled terms and/or semantic terms by displaying these controlled terms and/or semantic terms in a size that is proportional to their frequency of occurrence in the available data sets or data sources. In various aspects, the display 204 may be searchable via word search or natural language processing based on the controlled terms and/or semantic terms. In various aspects, the display 204 may illustrate only controlled terms and/or semantic terms, so that both the histogram 210 and the word density 220 display the relative frequency of use of individual controlled terms and/or semantic terms. In an embodiment, display 204 is an example user interface of a topic connection discovery platform.

Figure 2B:
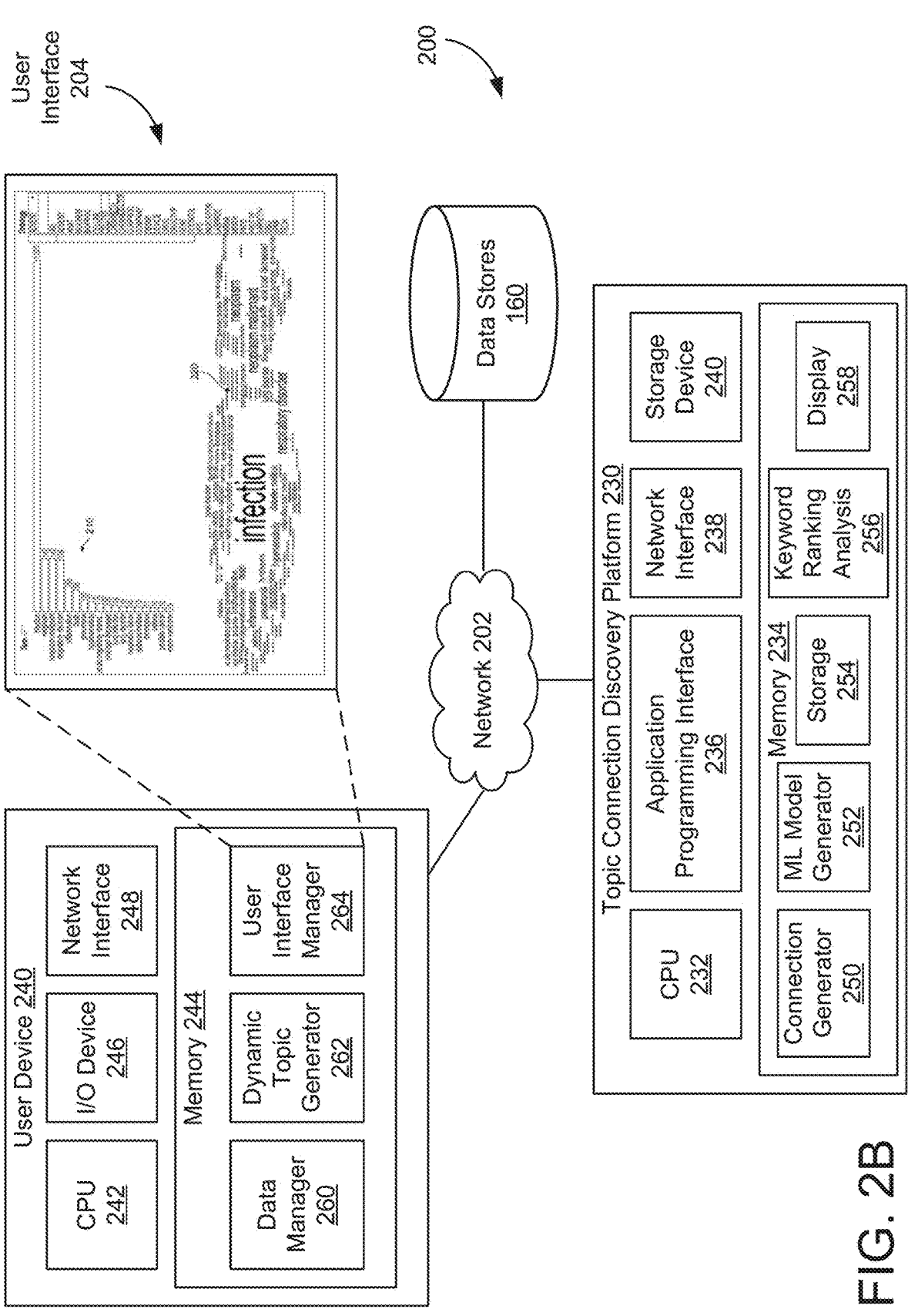
FIG. 2B is a high-level block diagram illustrating an example system for discovering topic connections, in accordance with various aspects.

FIG. 2B is a high-level block diagram illustrating an example system for discovering topic connections, in accordance with various aspects. FIG. 2B shows an embodiment of an example discovery system 200 with a user device 240 connected, through a network 202, to a topic connection discovery platform 230 for interacting with documents through a user interface 204 displayed on the user device 240. While some example features are illustrated, various other features have not been illustrated for the sake of brevity and so as not to obscure pertinent aspects of the example embodiments disclosed herein. In some embodiments, user device 240 and topic connection discovery platform 230 are computer-based components that may be interconnected by a network 202. Additional components of an example discovery system 200, such as data stores 160, may also be connected to network 202.

In some embodiments, one or more networks 202 may be used to communicatively interconnect various components of discovery system 200. For example, each component, such as user device 240, topic connection discovery platform 230 and data stores 160, may include one or more network interfaces and corresponding network protocols for communication over network 202. Network 202 may include a wired and/or wireless network (e.g., public and/or private computer networks in any number and/or configuration) which may be coupled in a suitable way for transferring data. For example, network 202 may include any means of a conventional data communication network such as a local area network (LAN), a wide area network (WAN), a telephone network, such as the public switched telephone network (PSTN), an intranet, the internet, or any other suitable communication network or combination of communication networks. In some embodiments, network 202 may comprise a plurality of distinct networks, subnetworks, and/or virtual private networks (VPN) may be used to limit communications among specific components. For example, user device 240 may be on a limited access network such that control data may only be transmitted between a user device 240 and topic connection discovery platform 230, enabling the topic connection discovery platform 230 to display documents through the user device 240 and enable real-time discovery of experiments, lab notebooks, pictures, PDF documents, or other documents through a graphical user interface (GUI).

User device 240 may be any suitable computer device, such as a computer, a computer server, a laptop computer, a tablet device, a netbook, an internet kiosk, a personal digital assistant, a mobile phone, a smart phone, a gaming device, or any other computing device. User device 240 is sometimes called a host, client, or client system. In some embodiments, user device 240 may host or instantiate one or more applications for interfacing with discovery system 200. For example, user device 240 may be a personal computer or mobile device running a scientific discovery application configured to provide a user interface for topic connection discovery platform 230. In some embodiments, user device 240 may be configured to access data accessible by the topic connection discovery platform 230 directly through network 202. In some embodiments, one or more functions of topic connection discovery platform 230 may be instantiated in user device 240 and/or one or more functions of user device 240 may be instantiated in topic connection discovery platform 230.

User device 240 may include one or more processors 242 for executing compute operations or instructions stored in memory 244 for accessing planning data and other functions of topic connection discovery platform 230 through network 202. In some embodiments, processor 242 may be associated with memory 244 and input/output device 246 for executing both data display operations and discovery system management operations. Processor 242 may include any type of processor or microprocessor that interprets and executes instructions or operations. Memory 244 may include a random access memory (RAM) or another type of dynamic storage device that stores information and instructions for execution by processor 242 and/or a read only memory (ROM) or another type of static storage device that stores static information and instructions for use by processor 242 and/or any suitable storage element. In some embodiments, user device 240 may allocate a portion of memory 244 and/or another local storage device (in or attached to user device 240) for storing discovery data for user device 240, such as topic data. In some embodiments, user device 240 may include one or more input/output (I/O) devices 246. For example, a graphical display, such as a monitor and/or touch screen display, and/or other user interface components such as a keyboard, a mouse, function buttons, speakers, vibration motor, a track-pad, a pen, voice recognition, biometric mechanisms, and/or any number of supplemental devices to add functionality to user device 240. Network interface 248 may include one or more wired or wireless network connections to network 202. Network interface 248 may include a physical interface, such as an ethernet port, and/or related hardware and software protocols for communication over network 202, such as a network interface card, wireless network adapter, and/or cellular data interface.

User device 240 may include a plurality of modules or subsystems that are stored and/or instantiated in memory 244 for execution by processor 242 as instructions or operations. For example, memory 244 may include a data manager 260 configured to provide a user interface for selectively creating, manipulating, and displaying real-time, near real-time, and/or stored structured data for planning in the topic connection discovery platform 230. Memory 244 may include dynamic topic generator 262 configured to dynamically generate topics responsive to user input received at a user interface 204. For example, a new topic may be generated based on a received user input that a selected keyword is associated with another keyword. Memory 244 may include a user interface manager 264 configured to provide a user interface 204 for generating, modifying, and displaying data received at user device 240. Memory 244 may include other modules, not illustrated, configured to perform functionality of the user interface 204, including rendering data values as graphical user interface elements such as control points, toggles, sliders, and grid selection interfaces.

Topic connection discovery platform 230 may include a housing and a bus interconnecting at least one processor 232, at least one memory 234, at least one storage device 240, and at least one interface, such as application programming interface 236 and/or network interface 238. The housing (not shown) may include an enclosure for mounting the various subcomponents of topic connection discovery platform 230, locating any physical connectors for the interfaces, and protecting the subcomponents. Some housings may be configured for mounting within a rack system. The bus (not shown) may include one or more conductors that permit communication among the components of topic connection discovery platform 230. Processor 232 may include any type of processor or microprocessor that interprets and executes instructions or operations. Memory 234 may include a random access memory (RAM) or another type of dynamic storage device that stores information and instructions for execution by processor 232 and/or a read only memory (ROM) or another type of static storage device that stores static information and instructions for use by processor 232 and/or any suitable storage element.

In some embodiments, topic connection discovery platform 230 may include application programming interface 236 configured to transfer data between the topic connection discovery platform 230, data stores 160, and/or a user device 240 through network 202. For example, application programming interface 236 may include functionality for data to be easily transferred between components of the discovery system 200. In some embodiments, topic connection discovery platform 230 may include multiple application programming interfaces 236 for communication with different types of applications on user devices 240 and/or data stores 160 over network 202.

Network interface 238 may include one or more wired or wireless network connections to network 202. Network interface 238 may include a physical interface, such as an ethernet port, and related hardware and software protocols for communication over network 202, such as a network interface card.

Storage devices 240 may include one or more non-volatile memory devices configured to store data, such as a hard disk drive (HDD), solid state drive (SSD), flash memory-based removable storage (e.g., secure data (SD) card), embedded memory chips, etc. In some embodiments, storage device 240 is, or includes, a plurality of solid-state drives.

In some embodiments, a respective data storage device 240 may include a single medium device, while in other embodiments the respective data storage device 240 includes a plurality of media devices. In some embodiments, media devices include NAND-type flash memory or NOR-type flash memory. In some embodiments, storage device 240 may include one or more hard disk drives. In some embodiments, storage devices 240 may include a flash memory device, which in turn includes one or more flash memory die, one or more flash memory packages, one or more flash memory channels or the like. However, in some embodiments, one or more of the data storage devices 240 may have other types of non-volatile data storage media (e.g., phase-change random access memory (PCRAM), resistive random access memory (ReRAM), spin-transfer torque random access memory (STT-RAM), magneto-resistive random access memory (MRAM), etc.).

Topic connection discovery platform 230 may include a plurality of modules or subsystems that are stored and/or instantiated in memory 234 for execution by processor 232 as instructions or operations. For example, memory 234 may include a connection generator subsystem 250 configured to generate connections between synonyms and topics for a dynamic topic generator 262 operating on user devices 240. Memory 234 may include a machine learning (ML) model generator subsystem 252 configured to generate machine learning models based on data received from data stores 160. Memory 234 may include a data storage subsystem 254 configured to store received data in storage device(s) 240 and/or data store 160 over the network 202. Memory 234 may include a keyword ranking analysis subsystem 256 configured to analyze keyword data for statistical metrics, such as repeating data values, and to rank the keywords based on the statistical metrics to form connections to a topic. Memory 234 may include a data display subsystem 258 configured to selectively display data on user device 240, which may be attached to topic connection discovery platform 230 or remotely connected via network 202. In some embodiments, the functions of ML model generator 252 may be integrated in topic connection discovery platform 230 and instantiated in memory 234 as a ML model generating subsystem and/or a subset of functions of keyword ranking analysis subsystem 256.

In some embodiments, discovery system 200 may include one or more remote and/or cloud-based resources for supporting the functions of topic connection discovery platform 230 and/or user device 240. For example, discovery system 200 may include a data store 160 configured to host some, all, or select portions of the storage functions of topic connection discovery platform 230, such as a cloud-based network attached storage system, distributed storage system, or on-premise data storage system. In some embodiments, the majority of functions described above for topic connection discovery platform 230 may reside in topic connection discovery platform 230 and select functions may be configured to leverage additional resources in a network server (not pictured) and/or data store 160. For example, a network server may be configured to support specialized and/or processing intensive numerical algorithms to supplement keyword ranking analysis subsystem 256, and/or data store 160 may be configured to support archiving of data for longer term storage.

Figure 3A:
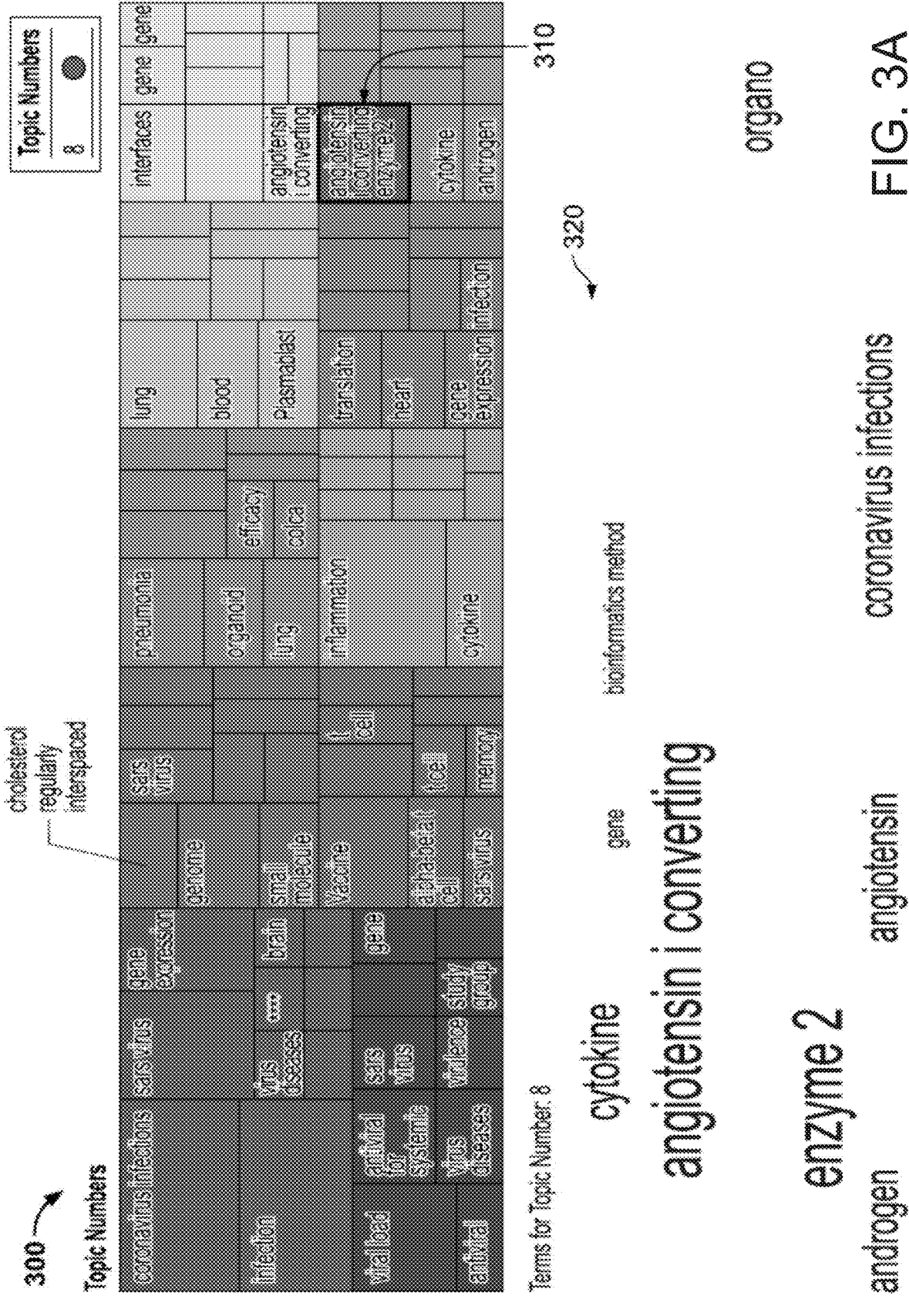
FIG. 3A is an illustration of a topic distribution in a plurality of data sources, in accordance with various aspects.

FIG. 3A is a display 300 illustrating a topic distribution in a plurality of data sources, in accordance with various aspects. For example, a topic may refer to any combination of controlled terms and/or semantic terms that define the topic. For example, a topic may be a specific combination of a drug, the disease that the drug is dedicating to mitigating, the recommended treatment to mitigate the disease, experimental reports such as scientific publications regarding the drug, disease or treatment, and the like. In various aspects, the various topics may be displayed on the selectable display 300 (i.e., a graphical user interface), and when one of the topics such as, e.g., topic 310, is selected, the various controlled terms and/or semantic terms 320 that constitute the topic 310 may be displayed. Accordingly, the list of controlled terms and/or semantic terms 320 that constitute a given topic is displayed when a given topic 310 is selected. In other aspects, the display 320 includes displaying terms at a size that is proportional to their frequency of occurrence in the available data sources, similarly to the display 220 discussed above with respect to FIG. 2A.

Figure 3B:
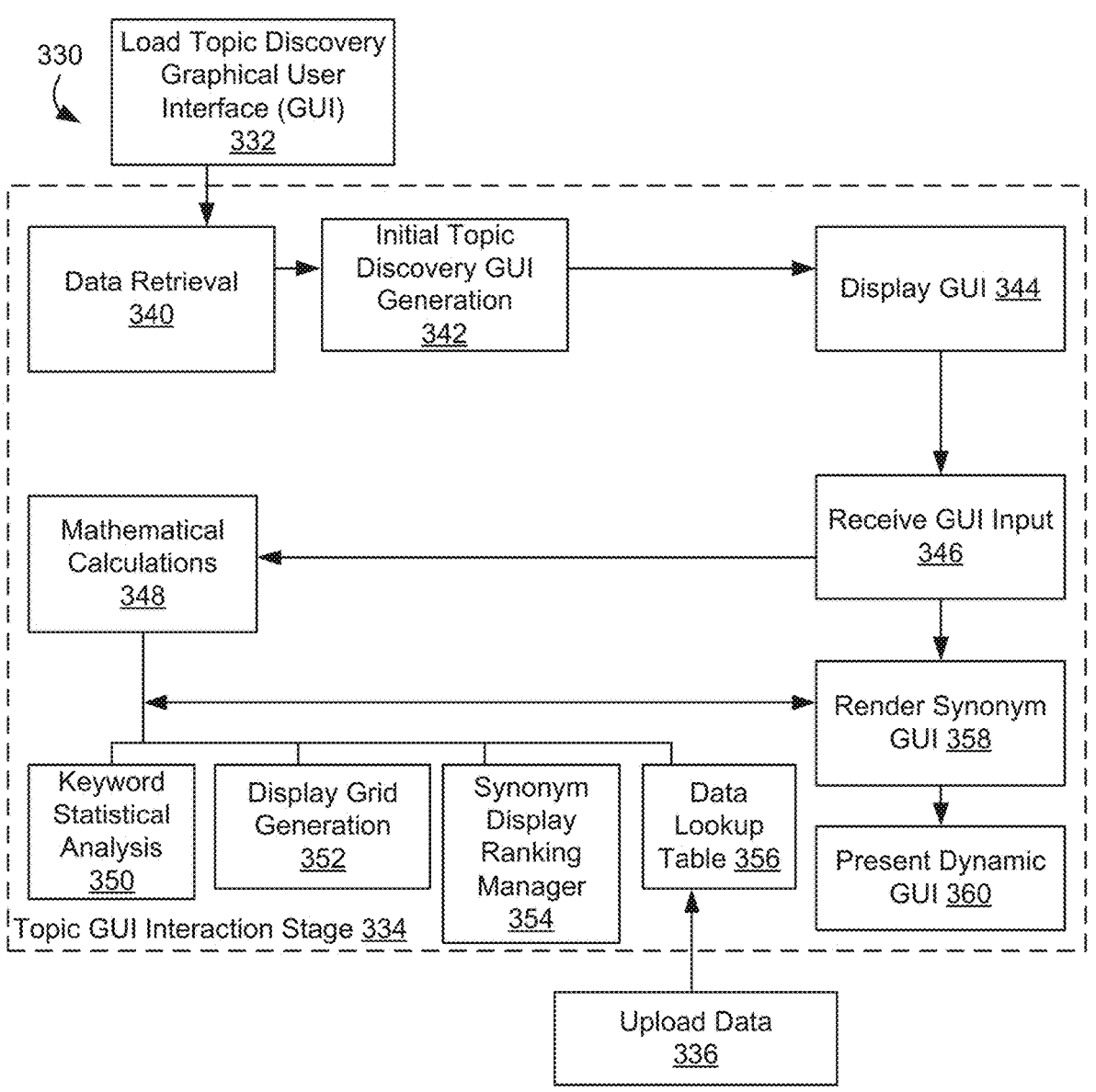
FIG. 3B is a high-level block diagram illustrating an example data flow of interacting with a topic discovery graphical user interface, in accordance with various aspects.

FIG. 3B schematically shows a topic GUI interaction stage that during normal operation that may be implemented in a computer-based discovery system 330, such as discovery system 200 in FIG. 2B. At block 332, a topic discovery graphical user interface (GUI) is loaded. For example, upon operation of discovery system 200, the topic discovery GUI is loaded on an application operating on a user device connected to the topic connection discovery platform. In some embodiments, the GUI is loaded with data from an existing project in the discovery system 330. In other embodiments, the GUI is loaded with data instantiated in memory.

In some embodiments, a topic GUI interaction stage 334 may be initiated during or after the topic discovery GUI has been loaded. For example, a topic connection discovery platform may be connected to discovery system 330 and/or instantiated in one of the components thereof. In some embodiments, the timing and length of topic GUI interaction stage 334 may be continuous based on the user input interactions with the user interface connected to the topic connection discovery platform.

In some embodiments, topic GUI interaction stage 334 may be completed only once. In some embodiments, topic GUI interaction stage 334 may be re-executed in response to events, changes, or updates that may change during data discovery (e.g., known data values, unexpected events, continuously updated data, data patterns emerging, etc.) that generate new connections based on keyword ranking, as described above with respect to FIG. 2B.

During topic GUI interaction stage 334, data may be retrieved at block 340. For example, the discovery system 330 may include data from an existing project that may be retrieved during or after the topic discovery GUI is loaded. At block 342, an initial topic discovery GUI may be generated. For example, the topic discovery GUI may include keywords corresponding to data values, a grid of the keywords, each box size in the grid illustrated based on frequency of keywords, and a numerical value corresponding to an aggregated count value of each keyword.

After the initial topic discovery GUI generation at block 342, the GUI may be displayed at block 344. For example, the GUI may include an interactive grid that shows the keyword data labels based on the topic connection discovery, color differentiation of groups of keywords, and a cluster node display GUI selectable by a user through the user interface on a user device connected to the discovery system 330 or instantiated in an interconnected topic connection discovery platform.

After the display of the GUI at block 344, GUI input may be received at block 346. For example, a grid block may be selected to display synonyms associated with a topic, as described above and illustrated with respect to FIG. 3A, where the control point may be selected via the user interface at the user device connected to the discovery system 330 or instantiated in an interconnected topic connection discovery platform. Additionally, other GUI input may be received at block 346, such as a user input to generate a cluster node GUI displaying documents related to a topic.

After receiving GUI input at block 346, mathematical calculations may be executed at block 348 to help render a topic discovery GUI at block 358. In some embodiments, mathematical calculations 348 may include keyword statistical analysis 350. For example, keyword statistical analysis may use mathematical calculations to determine a size and shape of grid boxes. The keyword statistical analysis 350 may include one or more modules to determine grid dimensions corresponding to the number of keywords counted in the documents.

In some embodiments, mathematical calculations 348 may include display grid generation 352. For example, display grid generation 352 may include a graphical method that draws different sized grid boxes in the GUI based on the GUI input received and the data values retrieved at block 340.

In some embodiments, mathematical calculations 348 may include a synonym display ranking manager 354. For example, keywords may correspond to synonyms of one or more controlled terms and/or semantic terms (e.g., gene, drug, disease, scientific publication, and the like), also referred to as a topic. The synonym display ranking manager 354 may assign a data value to a particular controlled term based on the number of related keywords connected to that term, or topic, as stored in a data table. In an embodiment, the retrieved data at block 340 may serve as an initial value for the number of keywords, based on existing data stored in memory, but as new documents and new connections are discovered to be connected to the topic, the synonym rankings may change based on the data value associated with the controlled term, consequently changing the display of synonyms within the topic discovery GUI. For example, a particular controlled term may be connected to a higher number of keywords for "COVID-19" based on a new document being uploaded as a data source. The synonym display ranking manager 354 may track the data values associated with the synonyms in the GUI.

In some embodiments, mathematical calculations 348 may include a data lookup table 356. For example, a data lookup table may be instantiated with data retrieved at block 340 to provide a baseline data set. In an embodiment, the data lookup table 356 may receive uploaded data at block 336. The data lookup table 356 may also be used to store various mathematical calculations 348, such as increases or decreases of the data values. Additionally, various constants and formulas may be used and stored with respect to the data lookup table 356 to work in conjunction with keyword statistical analysis 350, display grid generation 352, and/or synonym display manager 354.

Based on the mathematical calculations 348, a synonym GUI may be rendered at block 358. For example, the synonym GUI may include at least one of the following: the grid boxes displayed corresponding to the calculated data values of the display grid generation 352, depicting a grid box with a size proportional to the number of keywords counted in documents, color differentiation applied to different topics, a label appearing associated with the grid box based on the keyword it represents, and a word cloud depicting keywords in different font sizes based on number of keywords counted in documents, experiments, laboratory notebooks, attachments, and the like.

After the synonym GUI is rendered at block 358, the dynamic GUI is presented at block 360. This includes an updated data values corresponding to the size of grid boxes, the ordering of the grid boxes based on synonym display ranking, and color of a selected grid box modified based on the received GUI input at block 346. The topic GUI interaction stage 334 may repeat continuously as additional GUI input is received.

Figure 4:
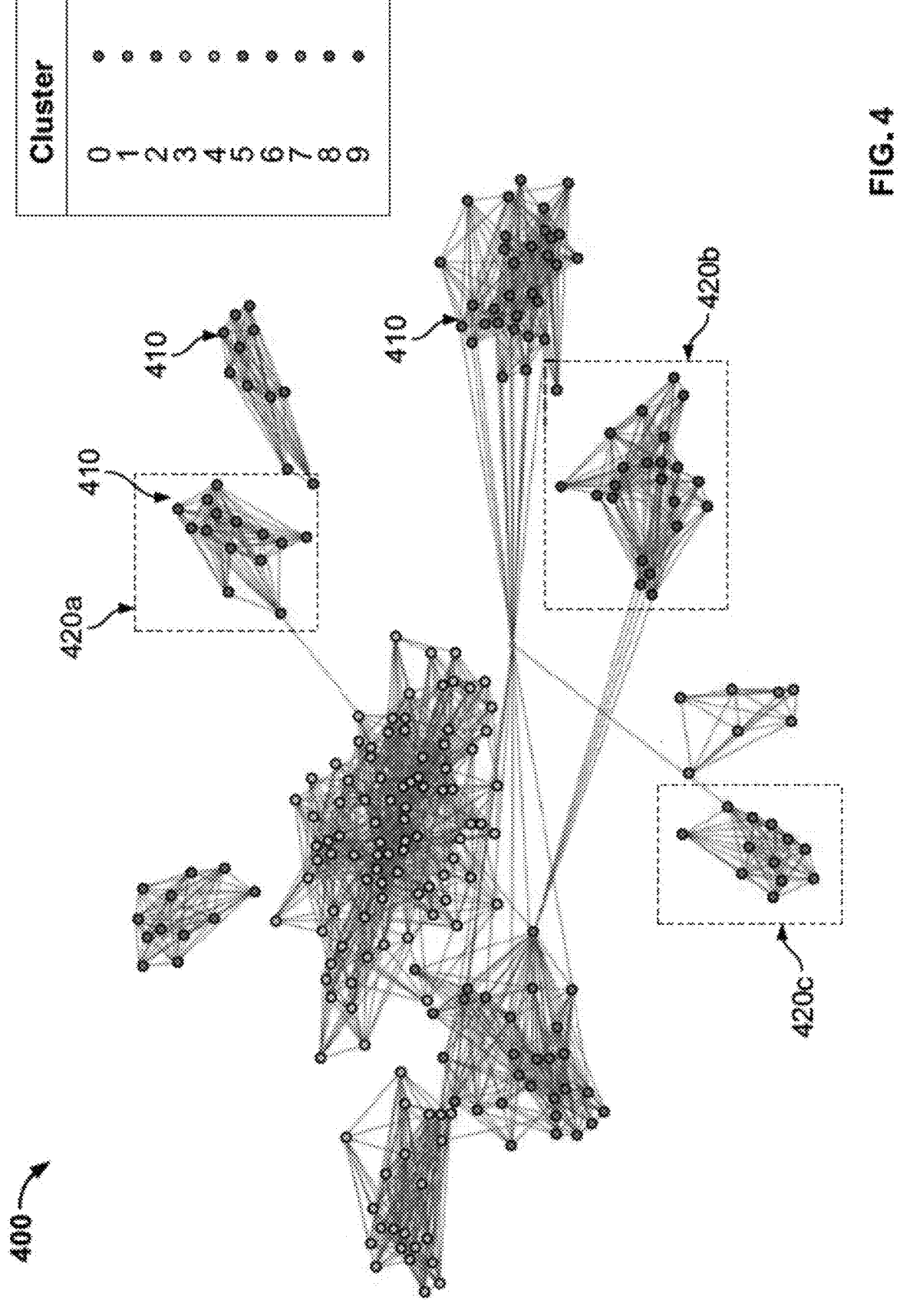
FIG. 4 is a schematic diagram illustrating clustered data items from different data sets, according to various aspects.

FIG. 4 is a schematic diagram illustrating clustered data items from different data sets, according to various aspects. In FIG. 4, the display 400 includes a plurality of clusters such as, e.g., clusters 420c, 420b and 420c of data items 410, the data items 410 in each cluster being from same or different data sets, according to various aspects. In FIG. 4, each colored dot in the display 400 represents a single data item 410. In various aspects, the data items 410 come from a number of different data sets, some of these data sets being separate and independent from each other. In various aspects, each data item 410 may be assigned one or more controlled terms and/or semantic terms, each semantic term or tag identifying a characteristic of the data item 410. For example, data item 410 may be assigned a tag that indicates that the data item 410 includes a gene, another tag that indicates that the data item 410 includes a drug, and yet another tag that indicates that the data item 410 includes an experimental protocol. In the example illustrated in FIG. 4, all data items that share the same controlled terms and/or semantic terms may be clustered together in a cluster such as, e.g., clusters 420a, 420b and 420c, and may be displayed in a same color.

In various aspects, a cluster may include a plurality of data items that share the same tags, the data items being provided from a variety of data sources. For example, cluster 420a may include data items that share the following tags:

a drug, a disease that the drug is typically used for, and a gene that is affected by the drug. Accordingly, it is possible to identify all the data items such as, e.g., publications, research papers, laboratory notebooks, research teams, and the like, that share the same combination of controlled terms and/or semantic terms, even if the various data items are spread in various parts of the world, or even if the research teams may be working on different projects. FIG. 4 allows a user or searcher to identify at a glance connections between various entities, research teams, and the like, even if the various entities were not aware of each other, and thus uncover previously unknown connections. Identifying these previously unknown connections may allow these entities to collaborate, exchange data and ideas, and generally promote and accelerate the research in the area defined by the combination of controlled terms and/or semantic terms of the cluster.

In various aspects, the data items 410 that are included in the cluster 420a are part of the cluster because they share a same combination of controlled terms and/or semantic terms (e.g., gene, drug, disease, scientific publication, and the like), also referred to as a topic. For example, with reference to FIG. 1 above, the data items 410 included in the cluster 420a may include controlled terms and/or semantic terms identifying a disease such as the disease referred to as "COVID-19," a disease such as "ovarian carcinoma" and "aneuploidy," this combination of controlled terms and/or semantic terms being included in, e.g., publications from a number of different research teams located in various parts of the world. Accordingly, because this specific combination of controlled terms and/or semantic terms, which make up a topic, may be common to a number of other data items, all the data items that share the same topic may be clustered in cluster 420a. Similarly, cluster 420b may include data items 410 that share a different topic or combination of controlled terms and/or semantic terms, and this other specific topic or combination of controlled terms and/or semantic terms may be common to a number of other data items. These other data items may thus be clustered in cluster 420b. In various aspects, the data items 410 may also be clustered based on a frequency of shared controlled terms and/or semantic terms in each data item. For example, a given cluster may include data items that discuss "COVID-19" a same number of times. In various aspects, the data items 410 in each cluster such as clusters 420a, 420b and 420c may be identified in a cluster-specific color. In various aspect, a same data item 410 may share different topics with different other data items, and may thus be represented in more than one cluster. In other aspects, a data item may only be illustrated in one cluster.

In various aspects, the display 400 may thus allow to de-silo information with respect to a given topic or combination of controlled terms and/or semantic terms (e.g., a drug used for a given disease using a given experiment) and to discover that, e.g., a research team in Puerto Rico and a research team in Holland are both included in the same cluster 420a because they both share the same topic or combination of tags. Such realization may have been unknown prior to establishing the display 400, and is thus a latent previously unknown relationship that is uncovered due to the display 400. Thus, FIG. 4 displays relationships between the various clusters 420a, 420b and 420c, including topics that the various data items may have in common, even when those relationships or connections were previously unknown. This is referred to as de-silo-ing the information. Once a relationship is found between, e.g., different data items or different clusters, the relationship may be further explored. Further exploration of a newly uncovered relationship may be achieved by, e.g., selecting, on the display, the various data items to obtain additional information on the data items, as further discussed below with respect to FIG. 5C. The example display 400 may be generated as part of a topic discovery GUI as illustrated in FIG. 3B and described above, in an embodiment.

Figure 5A:
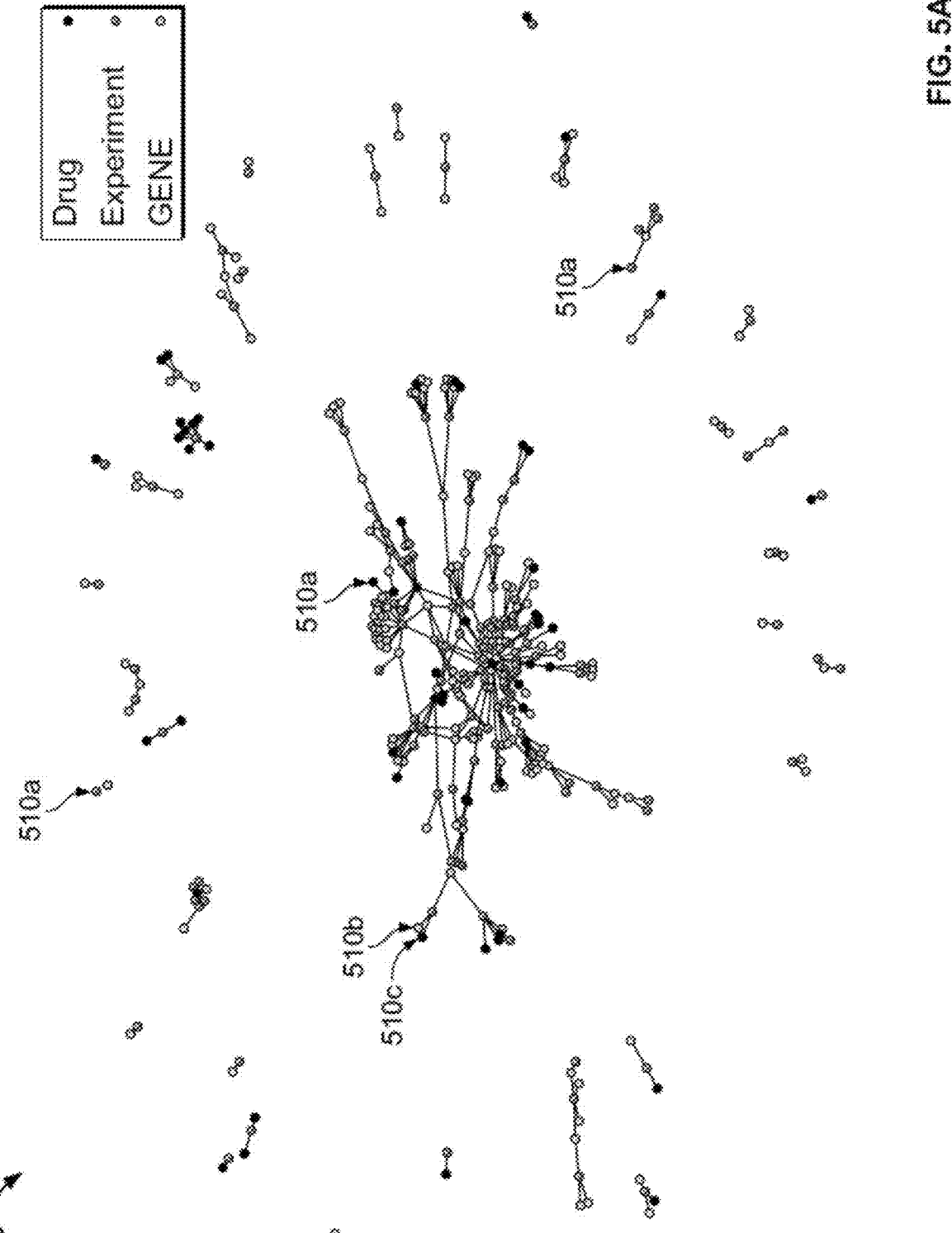
Figure 5B:
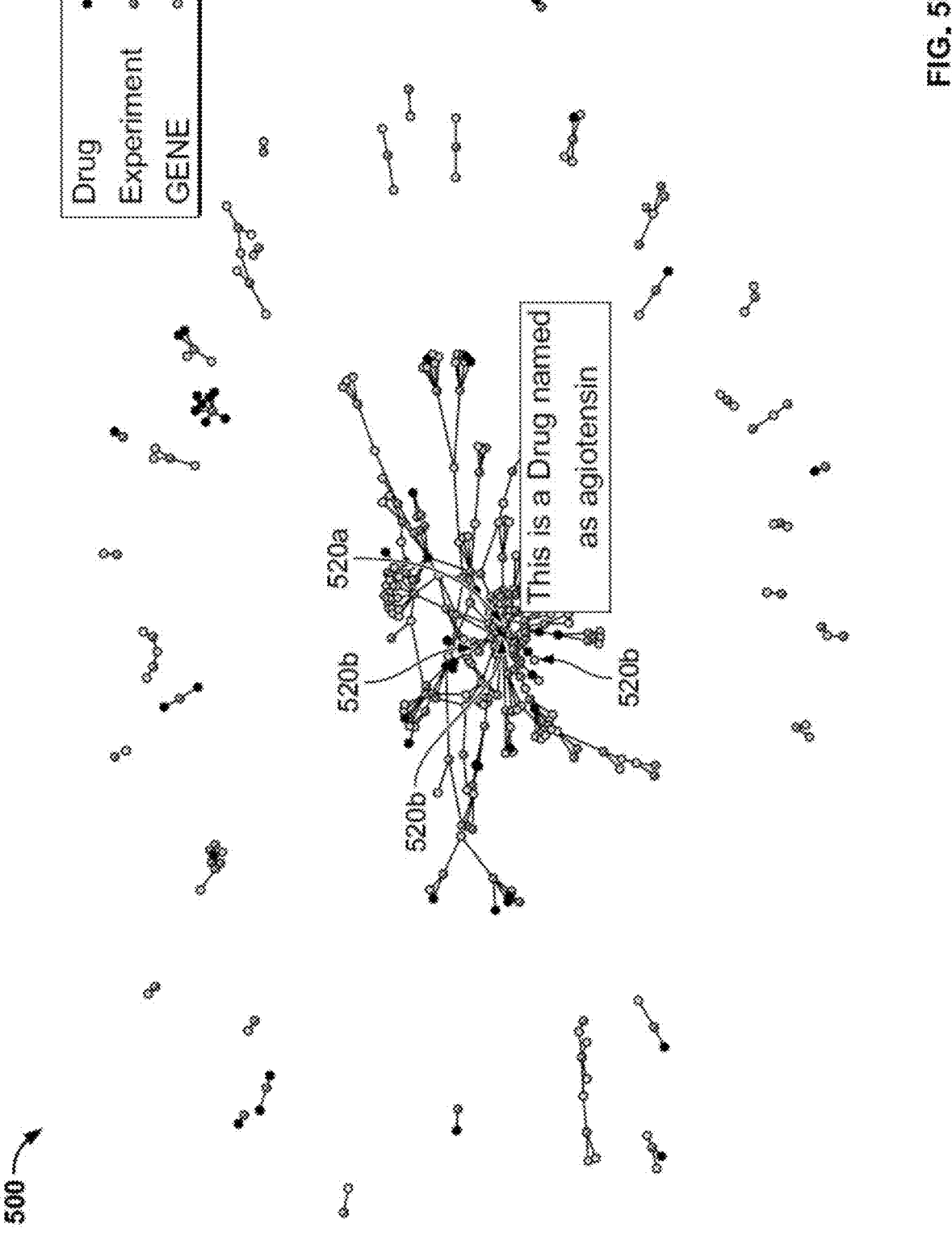

FIGS. 5A-5C are schematic diagrams illustrating a display 500 of data items from a plurality data sources, according to various aspects. In FIG. 5A, each colored dot in the display 500 represents a single data item 510a, 510b or 510c. In various aspects, the data items 510a, 510b or 510c are not clustered based on a shared number of controlled terms and/or semantic terms, or on a shared frequency of controlled terms and/or semantic terms, as discussed with respect to FIG. 4 above, but are displayed based on a degree of similarity with other data items. In various aspects, the degree of similarity between two data items may be determined by a number of controlled terms and/or semantic terms that they have in common. For example, the degree of similarity may be proportional to the number of controlled terms and/or semantic terms that they have in common. In various aspects, two data items that have a high degree of similarity with each other may be displayed at a close distance to one another, while two data items that have a low degree of similarity with each other may be displayed at a further distance from each other. FIG. 5A illustrates data items 510a, 510b or 510c that correspond to different semantic term types (e.g., drug, gene, experiment). In FIG. 5A, the data items 510a, 510b or 510c are displayed at distances to each other that are correlated to their respective degrees of similarity. FIGS. 5A-5C illustrate clusters that may be generated using one or more known clustering approaches, including but not limited to: centroid-based clustering, density-based clustering, distribution-based clustering, hierarchical clustering, and graph-based clustering. K-means is a centroid-based clustering algorithm that is used in FIGS. 5A-5C, though other clustering algorithms may be used. The clustering described herein relies on unsupervised machine learning, as described above in FIG. 2B.

In various aspects, the display of FIG. 5A may enable the possibility of uncovering relationships between data items that are not part of the same experimental data set, that are not produced by the same research team, or even that do not deal with the same disease or gene, based on the distances that separate them. For example, data items 510b and 510c may be part of different data sets and may be generated by different research teams or publications in various parts of the world. However, the fact that data items 510b and 510c are close to each other in the display 500 shows that there is a latent or previously unknown relationship between them. In aspects, this latent or previously unknown relationship, which is now uncovered in the display 500, may be worth further exploring by, e.g., increasing communications between those who generated the two data items 510b and 510c. For example, if data item 510b is a drug, and data item 510c is a disease, then it may be possible that the drug in 510b may be part of a possible treatment for the disease in 510c, even when there was no previous knowledge of any therapy for the disease in 510c that includes the drug in 510b.

Different types of distance metrics, or similarity, may be used in clustering, such as Euclidean distance, Manhattan distance, Chebyshev distance, Minkowski distance, Hamming distance, Cosine similarity, and Jaccard similarity. The examples described in FIGS. 5A-5C use Cosine similarity, but any valid metric that complies with a distance rule may be used.

As an illustrative example, a relationship may be uncovered between a disease (e.g., Covid) and a medical condition (e.g., breast cancer) which was not previously known or studied. Accordingly, a relationship between the data items representing the disease and the medical condition may be uncovered if the two data items are within close proximity to, or a short distance in display 500 from, each other. Discovering such a latent or previously unknown connection may open new avenues or research, cooperation and investigation towards treating the medical condition. Further exploration of a newly uncovered relationship may be achieved by, e.g., selecting, on the display, the various data items to obtain additional information on the data items, as illustrated in FIG. 5B. In FIG. 5B, the selected data item 520*a* is surrounded by a number of other data items 520*b* in close proximity thereto, and thus appears to be a relevant data item to data items 520*b*. In this example, the selected data item 520*a* is a drug named "angiotensin," and appears to have connections to a large number of genes and experiments in other data items 520*b*. In other aspects, further selecting the data item 520*a* may generate access to a data repository via, e.g., the internet, to obtain further information about the selected drug, as illustrated in FIG. 5C. In FIG. 5C, additional information relative to the selected data item 520*a* may be provided. The additional information may include, e.g., molecular formula, producing company, research papers associated therewith, treatment generally associated therewith, and the like. The display 500 in FIGS. 5A-5B may be generated as part of a topic discovery GUI as illustrated in FIG. 3B and described above, in an embodiment. The example user interface depicted in FIG. 5C may also be generated as part of a topic discovery GUI as illustrated in FIG. 3B and described above, in an embodiment.

Figure 6A:
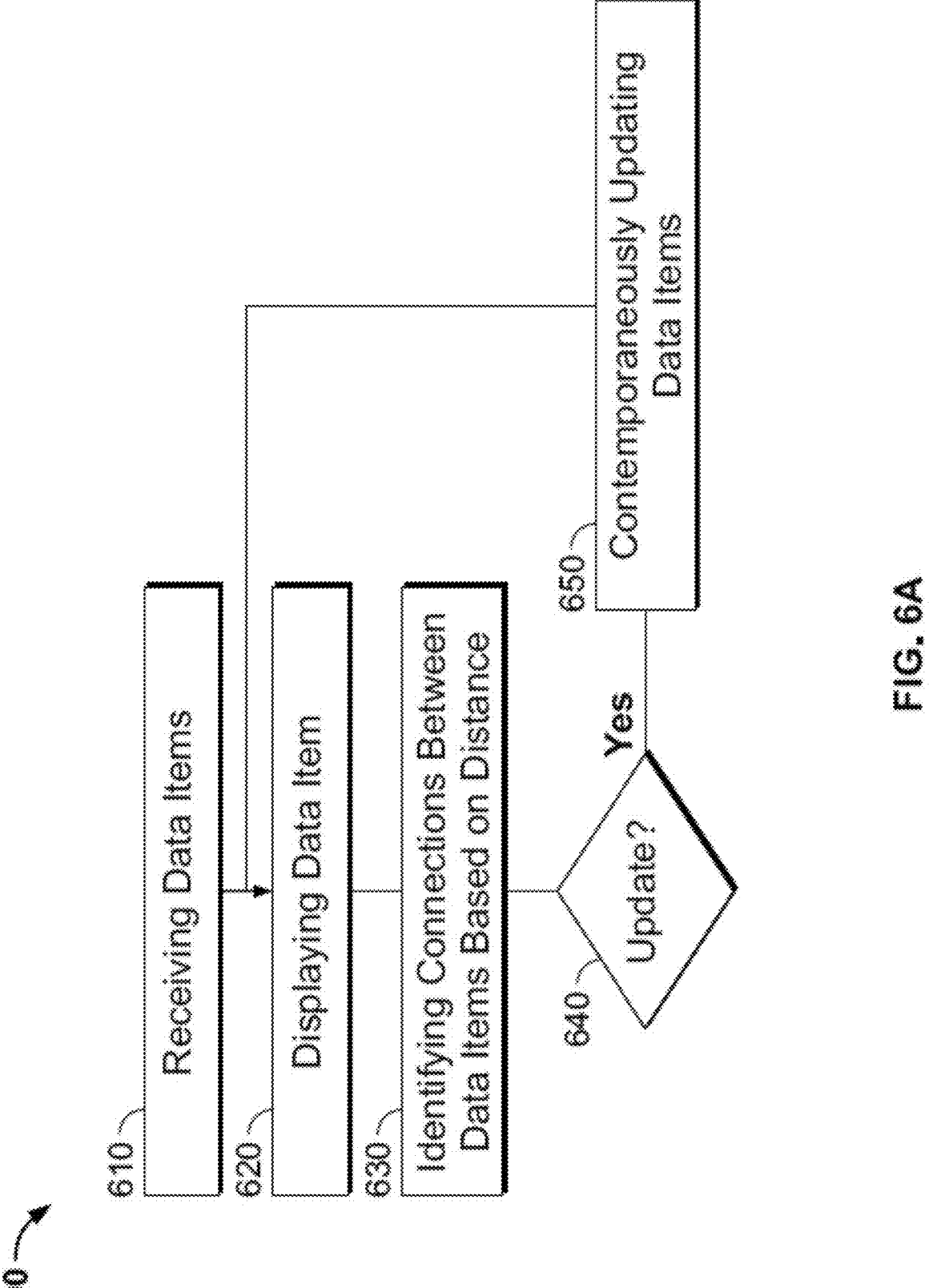
FIG. 6A is a flow chart depicting a method for identifying connections between data items in an updatable data repository, in accordance with various aspects.

FIG. 6A is a flow chart depicting a method for identifying connections between data items in an updatable data repository, in accordance with various aspects. For the sole purpose of convenience, method 600 is described through use of at least the example system 700 described below. However, it is appreciated that the method 600 may be performed by any suitable system.

Operation 610 includes dynamically receiving a plurality of data items from the updatable data repository. For example, the data items may be experimental results from different organizations, different researchers, or different publications, and may be stored in an updatable data repository. Specifically, operation 610 includes receiving a plurality of data items dynamically, where the contents of the data items may be updated in real time when the data items are updated at the source. In various aspects, the data items may include controlled terms and/or semantic terms defining the contents or characteristics thereof and providing a uniformity of terminology for the contents thereof. For example, the controlled terms and/or semantic terms may define a drug, an experiment, a gene, a device, a chemical molecule, a research center, a research team, a location, an event, or the like, in a manner that encompasses a number of synonyms, thus facilitating the search of the various data items. It should be noted that although the examples discussed above are discussed in the context of scientific research, various aspects are applicable to any other type of data item, publications such as, magazine publications, new publications, and the like, or any other type of data that is exchanged or published. Similarly, although research teams are discussed above, the data sets may be provided from any information-generating team such as news teams, investigations team, government organization, and the like. Also, although drugs are discussed above, any other class of objects, substances, services or products may also be sources of data items. In various aspects, the data items only include controlled terms and/or semantic terms.

Operation 620 includes displaying the dynamically received data items on a display. For example, the data items may be displayed as discussed above with respect to FIGS. 4 and 5. In various aspects, the data items may be grouped in clusters on the display, where all the members of a given cluster share a same combination and/or frequency of controlled terms and/or semantic terms, as discussed above with respect to FIG. 4. In other aspects, the data items may be displayed at specific distances from each other, the distances between correlated to a degree of similarity between the data items, as discussed above with respect to FIG. 5. For example, the higher the degree of similarity between two data items, the shorter the distance between them on the display. In aspects, the degree of similarity may be determined by the number of controlled terms and/or semantic terms that are shared by the data items, where the higher the number of shared controlled terms and/or semantic terms between two data items, the higher the degree of similarity therebetween. In other aspects, the degree of similarity may be determined by the frequency of shared controlled terms and/or semantic terms between the data items. For example, the display of the data items may be a two-dimensional display or a three-dimensional display.

Specifically, the degree of similarity between the displayed data items is determined based on the number or frequency of shared controlled or semantic terms between the data items. For example, when data items A and B share a higher number or frequency of controlled or semantic terms than data items A and C, then the degree of similarity between A and B is greater than the degree of similarity between data items A and C. As a result, the distance between displayed data items A and B may be smaller than the distance between displayed data items A and C.

Operation 630 includes identifying connections between data items from different updatable sources based on the display. In various aspects, during operation 630, identifying a connection between two data items may be based on the distance separating the two data items on the display. For example, a distance threshold may be defined, and a connection between any two data items may be identified when the distance separating the two data items is below the distance threshold. In various aspects, connections may be uncovered during an update of the data items in real time, where no connection was originally identified between two data items before the update, but became identifiable when at least one of the data items was updated, the update resulting in a shorter distance between the data items on the display such as, e.g., display 500 in FIG. 5, and thus possibly falling under the distance threshold for finding a connection.

Operation 640 includes determining whether any of the data items has been updated at the data source. If a data item has been updated such as, e.g., if an experimental protocol has been updated, then the data item that has been received during operation 610 is also updated in real time during operation 650.

During operation 650, according to various aspects, the data items which were dynamically received during operation 610 are updated contemporaneously, or in real time, when the data items themselves are updated at the data source. For example, if a given experimental protocol is updated at the source of the data items, such as, e.g., in the laboratory notebook of a given research team, then the data that is received during operation 610 is also updated in real time during operation 650. Accordingly, as a data item is updated, the display in operation 620 updates the location of the data item based on the update. As such, new distances may separate the data item from other data items, and new connections may be identified, in real time, as the result of the real time update of the data item. On the other hand, connections that were previously identified may now appear to be irrelevant after the data item update if the updated distances become greater than the distance threshold discussed in operation 630.

Figure 6B:
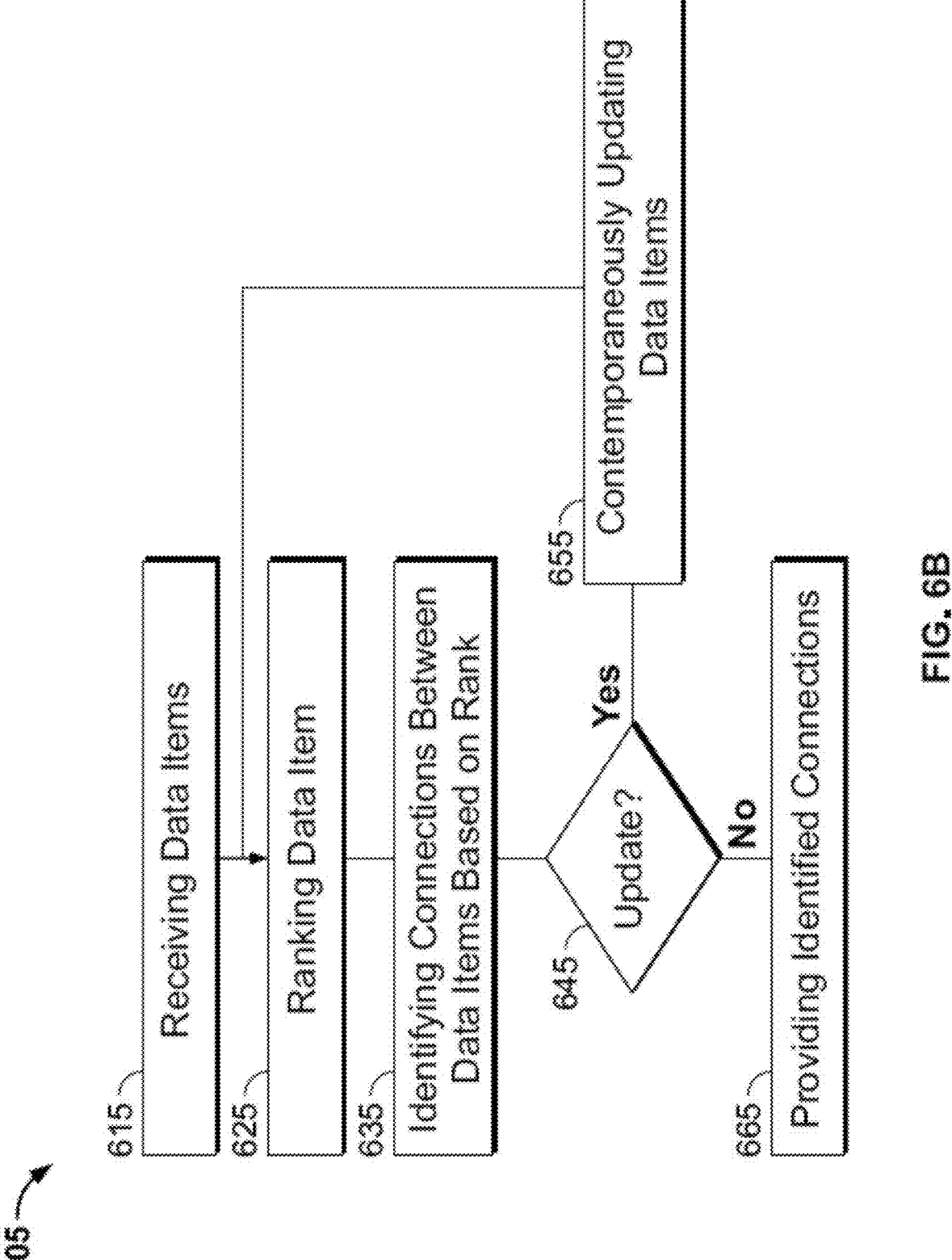
FIG. 6B is a flow chart depicting a method for identifying connections between data items in an updatable data repository, in accordance with various aspects.

FIG. 6B is a flow chart depicting a method for identifying connections between data items in an updatable data repository, in accordance with various aspects. For the sole purpose of convenience, method 605 is described through use of at least the example system 700 described below. However, it is appreciated that the method 605 may be performed by any suitable system.

Operation 615 includes dynamically receiving a plurality of data items from the updatable data repository. For example, the data items may be experimental results from different organizations, different researchers, or different publications, and may be stored in an updatable data repository. Specifically, operation 615 includes receiving a plurality of data items dynamically, where the contents of the data items may be updated in real time when the data items are updated at the source. In various aspects, the data items may include controlled terms and/or semantic terms defining the contents or characteristics thereof and providing a uniformity of terminology for the contents thereof. For example, the controlled terms and/or semantic terms may define data items in a manner that encompasses a number of synonyms, thus facilitating the search of the various data items. In various aspects, the data items only include controlled terms and/or semantic terms.

Operation 625 includes ranking the dynamically received data items with respect to each other. In various aspects, for each given data item, other data items are individually ranked with respect to the given data item based on the degree of similarity between the given data item and each of the other data items. For example, any two data items may be ranked with respect to each other based on the degree of similarity therebetween, and any two data items share the same rank. For example, the higher the degree of similarity between two data items, the higher the rank shared by them. In aspects, the degree of similarity may be determined by the number of controlled terms and/or semantic terms that are shared by the data items, where the higher the number of shared controlled terms and/or semantic terms between two data items, the higher the degree of similarity therebetween. In other aspects, the degree of similarity may be determined by the frequency of shared controlled terms and/or semantic terms between the data items.

Operation 635 includes identifying connections between data items from different updatable sources based on their respective ranks. In various aspects, during operation 635, identifying a connection between two data items may be based on the rank that the two data items share. For example, a rank threshold may be defined, and a connection between any two data items may be identified when the rank shared by the two data items is above the rank threshold. In various aspects, connections may be uncovered during an update of the data items in real time, where no connection was originally identified between two data items before the update, but became identifiable when at least one of the data items was updated, the update resulting in a higher rank between the data items, and thus possibly becoming higher than the rank threshold for finding a connection.

Operation 645 includes determining whether any of the data items has been updated at the data source. If a data item has been updated such as, e.g., if an experimental protocol has been updated, then the data item that has been received during operation 615 is also updated in real time during operation 655.

During operation 655, according to various aspects, the data items which were dynamically received during operation 615 are updated contemporaneously, or in real time, when the data items themselves are updated at the data source. For example, if a given experimental protocol is updated at the source of the data items, such as, e.g., in the laboratory notebook of a given research team, then the data that is received during operation 615 is also updated in real time during operation 655. Accordingly, as a data item is updated, the ranking operation 625 updates the rank between the data item and other data items based on the update. As such, new ranks may be shared by the data item and other data items, and new connections may be identified, in real time, as the result of the real time update of the data item. On the other hand, connections that were previously identified may now appear to be irrelevant after the data item update if the update rank becomes lower than the rank threshold discussed in operation 635.

Operation 665 includes providing the identified connections, or the identified updated connections. In various aspects, the connections, or the updated connections, may be provided to a third party such as, e.g., a user, a researcher, a data source, and the like.

Figure 7:
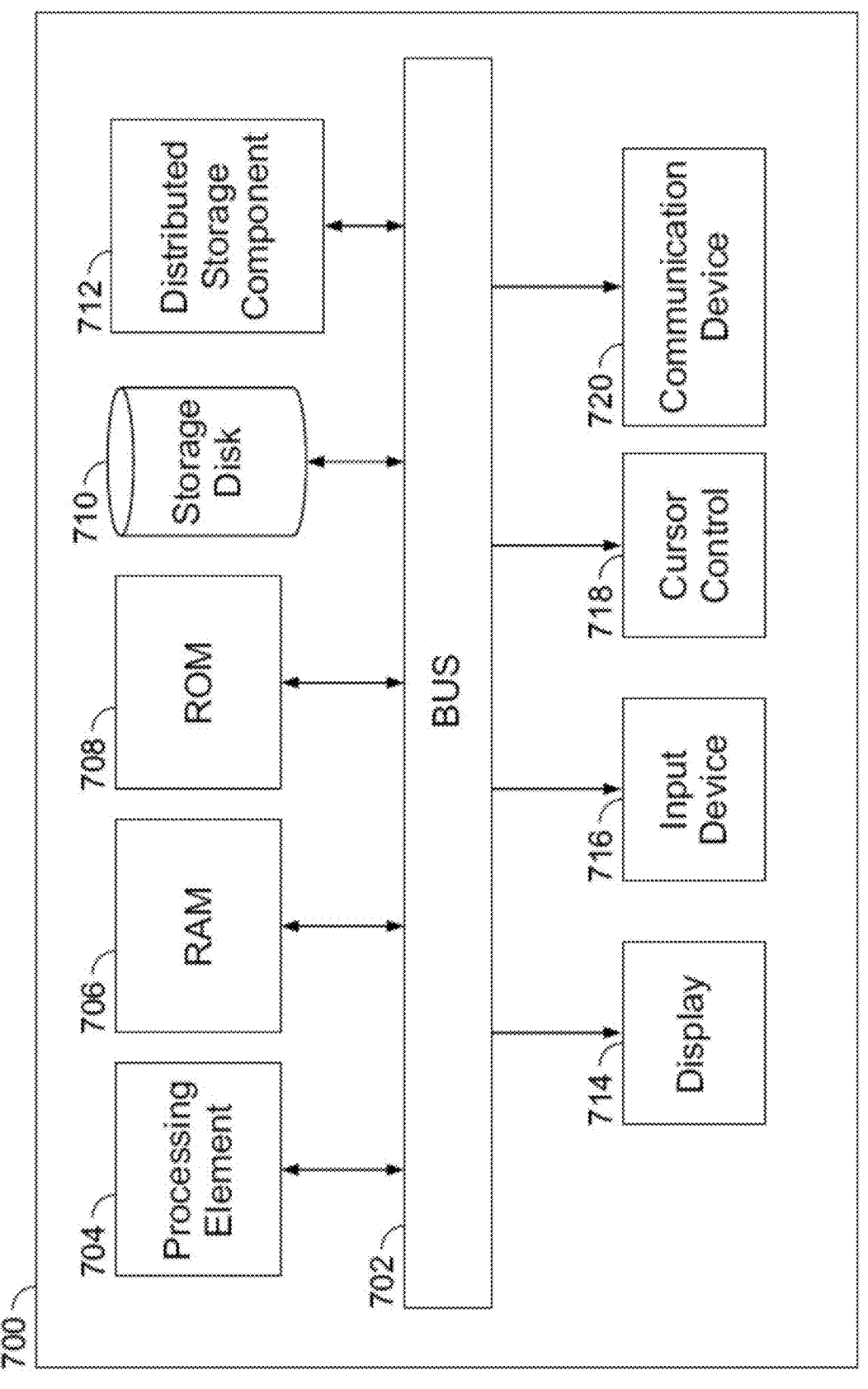
FIG. 7 depicts a block diagram of a computing device.

FIG. 7 depicts a block diagram of a computing device, according to various aspects. In the illustrated example, the computing device 700 may include a bus 702 or other communication mechanism of similar function for communicating information, and at least one processing element 704 (collectively referred to as processing element 704) coupled with bus 702 for processing information. As will be appreciated by those skilled in the art, the processing element 704 may include a plurality of processing elements or cores, which may be packaged as a single processor or in a distributed arrangement. Furthermore, a plurality of virtual processing elements 704 may be included in the computing device 700 to provide the control or management operations for the displays 400 and 500 or the methods 600 and 605 illustrated above.

The computing device 700 may also include one or more volatile memory(ies) 706, which can for example include random access memory(ies) (RAM) or other dynamic memory component(s), coupled to one or more busses 702 for use by the at least one processing element 704. Computing device 700 may further include static, non-volatile memory(ies) 708, such as read only memory (ROM) or other static memory components, coupled to busses 702 for storing information and instructions for use by the at least one processing element 704. A storage component 710, such as a storage disk or storage memory, may be provided for storing information and instructions for use by the at least one processing element 704. As will be appreciated, the computing device 700 may include a distributed storage component 712, such as a networked disk or other storage resource available to the computing device 700.

The computing device 700 may be coupled to one or more displays 714 for displaying information to a user. Optional user input device(s) 716, such as a keyboard and/or touchscreen, may be coupled to Bus 702 for communicating information and command selections to the at least one processing element 704. An optional cursor control or graphical input device 718, such as a mouse, a trackball or cursor direction keys for communicating graphical user interface information and command selections to the at least one processing element. The computing device 700 may further include an input/output (I/O) component, such as a serial connection, digital connection, network connection, or other input/output component for allowing intercommunication with other computing components and the various components of the displays 400 and 500 or the methods 600 and 605 discussed above.

In various embodiments, computing device 700 can be connected to one or more other computer systems via a network to form a networked system. Such networks can for example include one or more private networks or public networks, such as the Internet. In the networked system, one or more computer systems can store and serve the data to other computer systems. The one or more computer systems that store and serve the data can be referred to as servers or the cloud in a cloud computing scenario. The one or more computer systems can include one or more web servers, for example. The other computer systems that send and receive data to and from the servers or the cloud can be referred to as client or cloud devices, for example. Various operations of the displays 400 and 500 or the methods 600 and 605 may be supported by operation of the distributed computing systems.

The computing device 700 may be operative to control operation of the components of the displays 400 and 500 or the methods 600 and 605 through a communication device such as, e.g., communication device 720, and to handle data provided from the data sources as discussed above with respect to displays 400 and 500 or the methods 600 and 605. In some examples, analysis results are provided by the computing device 700 in response to the at least one processing element 704 executing instructions contained in memory 706 or 708 and performing operations on the received data items. Execution of instructions contained in memory 706 and/or 708 by the at least one processing element 704 can render the displays 400 and 500 or the methods 600 and 605 operative to perform methods described herein.

The term "computer-readable medium" as used herein refers to any media that participates in providing instructions to the processing element 704 for execution. Such a medium may take many forms, including but not limited to, non-volatile media, volatile media, and transmission media. Non-volatile media includes, for example, optical or magnetic disks, such as disk storage 710. Volatile media includes dynamic memory, such as memory 706. Transmission media includes coaxial cables, copper wire, and fiber optics, including the wires that include bus 702.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to the processing element 704 for execution. For example, the instructions may initially be carried on the magnetic disk of a remote computer. The remote computer can load the instructions into its dynamic memory and send the instructions over a telephone line using a modem. A modem local to computing device 700 can receive the data on the telephone line and use an infra-red transmitter to convert the data to an infra-red signal. An infra-red detector coupled to bus 702 can receive the data carried in the infra-red signal and place the data on bus 702. Bus 702 carries the data to memory 706, from which the processing element 704 retrieves and executes the instructions. The instructions received by memory 706 and/or memory 708 may optionally be stored on storage device 710 either before or after execution by the processing element 704.

In accordance with various embodiments, instructions operative to be executed by a processing element to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Figure 8:
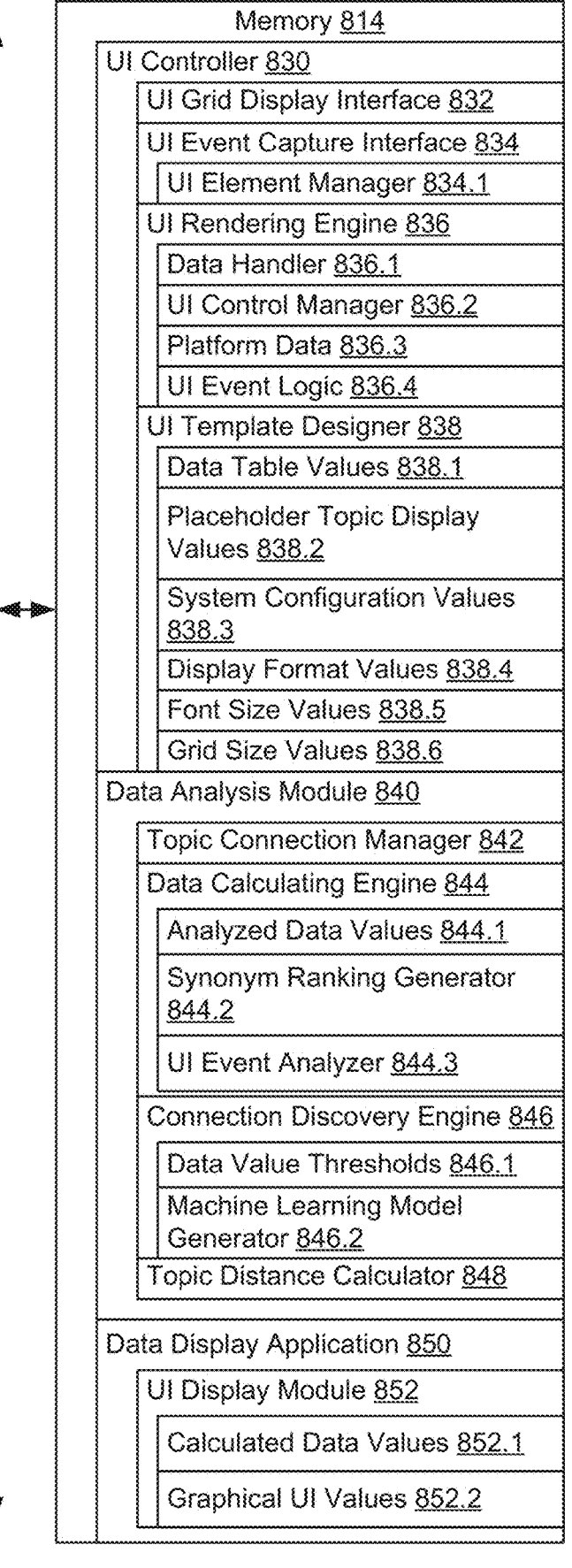
FIG. 8 schematically shows selected modules of a discovery system configured for dynamic topic connection discovery for unstructured data input.

FIG. 8 schematically shows selected modules of a discovery system 800 configured for dynamic topic connection discovery for unstructured data input. Discovery system 800 may incorporate elements and configurations similar to those shown in FIGS. 1A-3B. For example, discovery system 800 may be configured in a modeling platform similar to topic connection discovery platform 230. In some embodiments, one or more of the selected modules may access or be instantiated in the processors, memories, and other resources of user devices similar to user device 240. For example, a user device 240 and its embedded or attached compute resources may be configured with some or all functions of UI controller 830 to provide real-time user interface interaction with data values in a distributed fashion at the edge of discovery system 800 before selectively providing the data values to other system components, such as a data modeling platform, for additional analysis and/or use in a topic discovery application.

System 800 may include a bus 810 interconnecting at least one processor 812, at least one memory 814, and at least one interface, such as application programming interface 816 and network interface 818. Bus 810 may include one or more conductors that permit communication among the components of discovery system 800. Processor 812 may include any type of processor or microprocessor that interprets and executes instructions or operations. Memory 814 may include a random access memory (RAM) or another type of dynamic storage device that stores information and instructions for execution by processor 812 and/or a read only memory (ROM) or another type of static storage device that stores static information and instructions for use by processor 812 and/or any suitable storage element such as a hard disk or a solid state storage element. In some embodiments, processor 812 and memory 814 may be compute resources available for execution of logic or software instructions stored in memory 814 and computation intensive tasks, such as UI rendering engine 836, may be configured to monitor and share these resources.

Application programming interface 816 may be configured for connection with one or more user devices and/or data modeling platforms. For example, application programming interface 816 may include a software interface that enables data transfer and/or communications between applications operating on user devices 240 and/or topic connection discovery platform 230.

Network interface 818 may include one or more wired or wireless network connections to network, similar to network 202. Network interface 818 may include a physical interface, such as an ethernet port, and related hardware and software protocols for communication over the network, such as a network interface card or wireless adapter.

System 800 may include one or more non-volatile memory devices 820 configured to store data. For example, non-volatile memory devices 820 may include a plurality of flash memory packages organized as an addressable memory array and/or one or more solid state drives or hard disk drives. In some embodiments, non-volatile memory devices 820 may include a plurality of storage devices within, attached to, or accessible by a data modeling platform for storing and accessing data.

Discovery system 800 may include a plurality of modules or subsystems that are stored and/or instantiated in memory 814 for execution by processor 812 as instructions or operations. For example, memory 814 may include a UI controller 830 configured to control at least one user interface operating on a user device 240, capture and store user input from that user device, provide real-time analysis, and enable user access, such as through data display application 850. Memory 814 may include a data storage estimator configured to calculate an estimate of storage requirements based on usage. Memory 814 may include a data display application configured to provide a user interface for displaying and managing data values and/or discovery system 800.

User interface (UI) controller 830 may include interface protocols, functions, parameters, and data structures for connecting to and controlling user interfaces operating on user devices, capturing and storing data from those user interfaces, and interfacing with data analysis module 840 and data display application 850. For example, user interface controller 830 may be an application and/or corresponding hardware in a data modeling platform configured for network and/or direct communication with a set of associated user devices. UI controller 830 may be configured as a central point for data planning from the associated user devices that enables analysis of captured user input by analytics engines and presentation of transformed data to a user through data display application 850. In some embodiments, UI controller 830 may be divided among one or more data modeling platforms, server, and/or user device.

In some embodiments, UI controller 830 may include a plurality of hardware and/or software modules configured to use processor 812 and memory 814 to handle or manage defined operations of UI controller 830. For example, UI controller 830 may include a UI grid display interface 832, a UI event capture interface 834, a UI rendering engine 836, and a UI template designer 838.

UI grid display interface 832 may include UI interface protocols and a set of functions, parameters, and data structures for using, configuring, communicating with, and providing command messages to user interfaces on applications operating on user devices through application programming interface 816 and/or network interface 818. For example, UI grid display interface 832 may include an API and command set for interacting with applications in each user device to access one or more UI functions. In some embodiments, UI grid display interface 832 may be configured to set UI configuration parameters for UI elements, such as sliders, toggles, control points, lines connecting control points, and/or otherwise manage operation of user interfaces. For example, UI grid display interface 832 may maintain a UI configuration table, pages, or similar data structures that includes entries for each user interface being managed and their respective user device-specific configuration parameters, active control features, and other configuration and control information for managing the user interfaces.

UI event capture interface 834 may include interface protocols and a set of functions, parameters, and data structures for receiving UI event data from associated user devices and/or user interfaces. For example, UI event capture interface 834 may include data channels and related data buffers for managing a plurality of user interface events. In some embodiments, each user interface may a dedicated data channel for continuously and/or selectively sending its event data to UI event capture interface 834. For example, received UI event data may be buffered by UI event capture interface 834 before being transported to UI rendering engine 836, UI template designer 838, and data analysis module 840. In some embodiments, UI event capture interface 834 may be configured to transport data to the data analysis module 840 during a topic GUI interaction stage. In some embodiments, UI event capture interface 834 may receive or generate data based on received data analysis.

In some embodiments, UI event capture interface 834 may include a UI element manager 834.1 configured to identify and manage the UI elements sending UI event data from the user devices. For example, UI element manager 834.1 may manage status and state of each UI element. In some embodiments, UI element manager 834.1 may selectively send data to data analysis module 840 for data analysis to identify data value patterns and/or provide a notification to data analysis module 840 of the availability and storage location of data for analysis in non-volatile memory 820. In some embodiments, UI element manager 834.1 may include configurable UI elements. For example, a synonym GUI, a grid of selectable boxes, histogram, a cluster of nodes, a word cloud, and other UI elements may each be configured for specific processing, priority, and timing, including selective allocation of compute resources to support each UI element.

UI rendering engine 836 may include one or more rendering algorithms and a set of functions, parameters, and data structures for processing user input received from associated user devices and/or user interfaces to enable real-time or near-real-time response to received user input, where the response is a graphical rendering of the UI element responsive to the received user input. In some embodiments, UI rendering engine 836 may include a data handler 836.1 configured to determine different types of data represented by UI elements and incorporate methods of handling the data accordingly.

In some embodiments, data handler 836.1 may be configured for one or more data types, sometimes referred to as a data class, such as documents, experiments, laboratory notebooks, attachments, etc. Data handler 836.1 may interact with a UI control manager 836.2, such as a software module to track and manage status of UI controls. In some embodiments, UI rendering engine 836 may be configured for a plurality of data types and include data handlers trained to each data type. Data handler 836.1 may be configured to interact with other data including platform data 836.3. For example, platform data 836.3 may include position information of UI elements, such as rendering canvas coordinates, graphical information regarding icons and other visual elements, and data type or class. UI event logic 836.4 may include a plurality of event conditions based on detected data objects and whether other systems or subsystems should be notified of the UI event. These event conditions may include logical evaluation of one or more parameters from the output data, generally comparing output data parameters to corresponding UI event threshold parameters for determining a UI event. As another example, UI event logic 836.4 may include descriptive information of a UI event occurring, such as a recognized hand gesture, a recognized user input on a UI control, such as dragging a UI element upwards, downwards, or in other directions. In some embodiments, UI control manager 836.2 may interact with control UI data 820.2 stored in non-volatile memory 820, such as graphical icon data for rendering purposes. In some embodiments, platform data 836.3 may be stored as configuration values 820.3 in non-volatile memory 820, such as a data table of metadata tags associated with uploaded data 420.1.

UI template designer 838 may enable the template design of a user interface (UI) to represent data table values 838.1 corresponding to the placeholder topic display values 838.2 from a data table 820.4 stored in non-volatile memory 820. For example, uploaded data 820.1 may be copied to a data table 820.4 such that placeholder topic display values 838.2 may be generated, such as various topic labels already discovered in the data set. The placeholder topic display values 838.2 may be generated by data analysis module 840 having a data calculating engine 844 to create analyzed data values 844.1. For example, the uploaded data 820.1 may include data representing terms in documents, represented as a term-document matrix. Using system configuration values 838.3, which may, in some embodiments, correspond to configuration values 820.3 stored in non-volatile memory 820, the UI template designer 838 may identify an initial set of keywords for display in a grid, such as the grid depicted in FIG. 3A. In some embodiments, display format values 838.4 may be received via a user device connected through a network interface 818 and stored in configuration values 820.3 in non-volatile memory 820. For example, different user devices have display format values 838.4, such as screen resolution, number of pixels, screen dimensions, etc.

In some embodiments, UI template designer 838 may be configured to generate font size values 838.5 as calculated by data calculating engine 844 in the data analysis module 840 based on the number of keywords counted in the document set and further configured to determine grid size values 838.6 proportional to the number of keywords. For example, as shown in FIG. 3A, "coronavirus infections" is a label included in the top-left grid box with grid size values 838.6 proportional to the number of counted keywords associated with the label (or topic). The same label "coronavirus infections" is listed in the word cloud GUI in a font size proportional to the number of counted keywords, when compared with the other keywords listed in the word cloud GUI. Thus, the font size values 838.5 may be reflected in the font sizes of topics displayed in the word cloud GUI, as stored in the non-volatile memory 820. Grid size values 838.6, in this example, may refer to the different dimensions of each grid box in the grid, as shown in FIG. 3A.

In some embodiments, UI event logic 836.4 may include logical rules configured to trigger data analysis from the data analysis module 840. For example, UI event logic 836.4 may be embodied in a rules engine that receives and/or maintains state information for UI elements and data analysis of data table values 838.1, font size values 838.5, grid size values 838.6 and/or placeholder topic display values 838.2 to determine colors, sizes of grid boxes, font sizes of labels and/or other data analysis responsive to user input at the UI event capture interface 834. In some embodiments, UI event logic 836.4 may be configured to determine events that are used as triggers for generating various graphical user interface displays, such as cluster-node GUI display, grid GUI display, and word cloud GUI display. For example, user input received at the UI event capture interface 834 may indicate the user selecting a topic in the GUI display. This selection may trigger UI event logic 836.4 to display various GUIs using the UI event analyzer 844.3 and the data analysis module 840. Additionally, analyzed data values 844.1 may be presented through the topic connection manager 842. Additionally, the synonym ranking generator 844.2 may be used to identify a ranking of synonyms where the ranking determines a position of a synonym represented in a GUI as a word or grid box higher than lower ranked synonyms. Additionally, as described above, the topic connection manager 842 may generate new nodes in a cluster GUI, where the new nodes each represent a document that has been recently uploaded that have counted keywords that are associated with the topic, where the cluster represents the topic. In some embodiments, UI event logic 836.4 may generate an event notification and send it over a network to data display application 850 to automatically generate new topic connections based on the unsupervised machine learning of the clustering algorithm.

Data analysis module 840 may include a plurality of hardware and/or software modules configured to use processor 812 and memory 814 to handle or manage defined operations of data analysis module 840. For example, data analysis module 840 may include a topic connection manager 842, data calculating engine 844, connection discovery engine 846, and topic distance calculator 848.

Topic connection manager 842 may include data interface protocols and a set of functions, parameters, and data structures for managing the connections between synonyms and topics based on thresholds, as described above and depicted in the related figures. Returning to FIG. 5A, each colored dot in the display 500 represents a single data item 510a, 510b or 510c. In various aspects, the data items 510a, 510b or 510c are not clustered based on a shared number of controlled terms and/or semantic terms, or on a shared frequency of controlled terms and/or semantic terms, as discussed with respect to FIG. 4 above, but are displayed based on a degree of similarity with other data items. In various aspects, the degree of similarity between two data items may be determined by a number of controlled terms and/or semantic terms that they have in common. For example, the degree of similarity may be proportional to the number of controlled terms and/or semantic terms that they have in common. In various aspects, two data items that have a high degree of similarity with each other may be displayed at a close distance to one another, while two data items that have a low degree of similarity with each other may be displayed at a further distance from each other.

FIG. 5A illustrates data items 510a, 510b or 510c that correspond to different semantic term types (e.g., drug, gene, experiment). In FIG. 5A, the data items 510a, 510b or 510c are displayed at distances to each other that are correlated to their respective degrees of similarity. For each given data item, other data items are individually ranked with respect to the given data item based on the degree of similarity between the given data item and each of the other data items. For example, any two data items may be ranked with respect to each other based on the degree of similarity therebetween, and any two data items share the same rank. For example, the higher the degree of similarity between two data items, the higher the rank shared by them. In aspects, the degree of similarity may be determined by the number of controlled terms and/or semantic terms that are shared by the data items, where the higher the number of shared controlled terms and/or semantic terms between two data items, the higher the degree of similarity therebetween. In other aspects, the degree of similarity may be determined by the frequency of shared controlled terms and/or semantic terms between the data items. Returning to an illustrative example described above, a relationship may be uncovered between a disease (e.g., Covid) and a medical condition (e.g., breast cancer) which was not previously known or studied. Accordingly, a relationship between the data items representing the disease and the medical condition may be uncovered if the two data items are within close proximity to, or a short distance in display 500 from, each other. Discovering such a latent or previously unknown connection may open new avenues or research, cooperation and investigation towards treating the medical condition. Further exploration of a newly uncovered relationship may be achieved by, e.g., selecting, on the display, the various data items to obtain additional information on the data items, as illustrated in FIG. 5B. In FIG. 5B, the selected data item 520*a* is surrounded by a number of other data items 520*b* in close proximity thereto, and thus appears to be a relevant data item to data items 520*b*. The topic connection manager 842 manages the connections between data items from different updatable sources based on the display. Accordingly, as a data item is updated, the display in operation 620 (as shown in FIG. 6A) updates the location of the data item based on the update. As such, new distances may separate the data item from other data items, and new connections may be identified, in real time, as the result of the real time update of the data item. On the other hand, connections that were previously identified may now appear to be irrelevant after the data item update if the updated distances become greater than the distance threshold discussed in operation 630.

In some embodiments, data analysis module 840 may include a data calculating engine 844 for generating data calculations in collaboration with the received user input from the UI event capture interface 834. For example, data calculating engine 844 may rely on analyzed data values 844.1 to calculate related graphical data points for a cluster GUI as determined by a topic distance calculator 848. As another example, data calculating engine 844 may rely on analyzed data values 844.1 to calculate related graphical grid size values 838.6 for a grid GUI based on the system configuration values 838.3 and display format values 838.4. In some embodiments, data calculating engine 844 may include a UI event analyzer 844.3 for analyzing the status of UI elements from the UI element manager 834.1 and use UI event logic 836.4 to determine positions and font sizes of terms in a word cloud GUI, as described above.

Connection discovery engine 846 may include data interface protocols and a set of functions, parameters, and data structures for using machine learning to discover connections between synonyms and topics based on thresholds, as described above and depicted in FIGS. 6A-6B. Identifying a connection between two data items may be based on the rank that the two data items share. For example, a rank threshold may be pre-defined, and a connection between any two data items may be identified when the rank shared by the two data items is above the rank threshold. In various aspects, connections may be uncovered during an update of the data items in real time, where no connection was originally identified between two data items before the update but became identifiable when at least one of the data items was updated, the update resulting in a higher rank between the data items, and thus possibly becoming higher than the rank threshold for finding a connection.

Data display application 850 may include data interface protocols and a set of functions, parameters, and data structures for managing display of data at a user device through a user interface for a viewing user to continue interacting and viewing unstructured data for topic discovery purposes. For example, data display application 850 may operate a user interface upon which a UI controller 830 generates a UI grid display interface 832 and uses a UI event capture interface 834 to record user input. In some embodiments, uploaded data 820.1 appears on the data display application 850 as an interactive grid interface. Additionally, the UI rendering engine 836 manages the rendering of the user interface on the data display application 850. For example, discovery system 800 may support continuous display and/or capture of user input at the user interface on a user device operating the data display application 850. The UI display module includes, in some embodiments, calculated data values 852.1 from the data calculating engine 844 and graphical UI values 852.2 from the UI rendering engine. In some embodiments, configuration values 820.3 are used by the data display application 850 to generate a user interface that is correctly formatted for the user device.

Data display application 850 may include interface protocols, functions, parameters, and data structures for providing a user interface for generating and modifying data planning and/or displaying data in the discovery system 800, such as through UI controller 830. For example, data display application 850 may be a software application running on a user device integral to, connected to, or in network communication with UI controller 830 and/or a data modeling platform. In some embodiments, data display application 850 may run on a separate computing device from UI controller 830, such as a personal computer, mobile device, or other user device. In some embodiments, data display application 850 may be configured to interact with APIs presented by an access/display manager.

In some embodiments, data display application 850 may include a plurality of hardware and/or software modules configured to use processor 812 and memory 814 to handle or manage defined operations of data display application 850. For example, data display application 850 may include a UI display module 852.

The UI display module 852 may include a set of functions, parameters, and data structures for navigating and displaying data generated through UI controller 830. For example, the UI display module 852 may include a graphical user interface and interactive controls for displaying lists, tables, thumbnails, or similar interface elements for selecting and displaying data for various purposes. In some embodiments, the UI display module 852 may enable split screen display of multiple datasets. This would enable a viewing user to identify different scenarios with different topics that have been connected based on the underlying data, as illustrated in FIGS. 5A-5B.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method for identifying connections between data items in an updatable data repository, the method comprising:

dynamically receiving a plurality of data items from the updatable data repository, the data items being provided by a plurality of updatable sources, each data item including one or more controlled terms;

determining one or more topics based on the one or more controlled terms, each topic comprising a specific combination of controlled terms using unsupervised machine learning and non-negative matrix factorization;

displaying the dynamically received data items and the one or more determined topics on a display;

receiving a selection of a topic of the one or more topics on a user interface on the display; and identifying one or more connections between two or more data items of the plurality of data items from different updatable sources based on the two or more data items being associated with the selection of the topic of the one or more determined topics;

wherein the dynamically received data items are updated contemporaneously when the sources thereof are updated.

2. The method of claim 1, wherein, for each data item, each controlled term defines one or more characteristics of the data item.

3. The method of claim 2, wherein the one or more characteristics comprise at least one of a drug, an experiment, a gene, a device, a chemical molecule, a research center, a research team, a location, and an event.

4. The method of claim 1, wherein the data items only comprise controlled terms.

5. The method of claim 1, wherein:

the displayed data items are separated by distances related to a degree of similarity therebetween; and identifying the one or more connections is based on the distances.

6. The method of claim 1, wherein a degree of similarity between two data items is defined by at least one of a number and a frequency of controlled terms shared by the two data items.

7. The method of claim 1, further comprising:

defining a distance threshold;

wherein identifying the one or more connections comprises identifying data items that are separated by a distance that is less than the distance threshold.

8. The method of claim 1, wherein the data items are grouped in one or more clusters on the display, the data items in each cluster sharing one of same controlled terms and same frequency of controlled terms.

9. The method of claim 1, wherein the updatable data repository comprises one or more laboratory electronic notebooks.

10. The method of claim 1, wherein when the dynamically received data items are updated, at least one connection is identified as a result thereof.

11. A data connection finder comprising:

a data receiver;

an updatable data repository functionally coupled to the data receiver;

a display device functionally coupled to the data receiver;

a processor operatively coupled to the data receiver, to the updatable data repository and to the display device; and a memory coupled to the processor, the memory storing instructions that, when executed by the processor, perform a set of operations comprising:

dynamically receiving, at the data receiver, a plurality of data items from the updatable data repository, the data items being provided by a plurality of updatable sources, each data item including one or more controlled terms;

determining one or more topics based on the one or more controlled terms, each topic comprising a specific combination of controlled terms using unsupervised machine learning and non-negative matrix factorization;

displaying the dynamically received data items on a display of the display device;

receiving a selection of a topic of the one or more topics on a user interface on the display; and identifying, via the processor, one or more connections between two or more data items of the plurality of data items from different updatable sources based on the two or more data items being associated with the selection of the topic of the one or more determined topics;

wherein the dynamically received data items are updated contemporaneously when the sources thereof are updated.

12. The data connection finder of claim 11, wherein:

the displayed data items are separated, on the display of the display device, by distances related to a degree of similarity therebetween; and identifying the one or more connections is based on the distances.

13. The data connection finder of claim 11, wherein a degree of similarity between two data items is defined by at least one of a number and a frequency of controlled terms shared by the two data items.

14. The data connection finder of claim 11, wherein the set of operations further comprise:

defining a distance threshold;

wherein identifying the one or more connections comprises identifying data items that are separated by a distance that is less than the distance threshold.

15. The data connection finder of claim 11, wherein:

the data items are grouped, on the display of the display device, in one or more clusters; and the data items in each cluster share same controlled terms.

16. The data connection finder of claim 11, wherein the updatable data repository comprises one or more electronic workbooks.

17. The data connection finder of claim 11, wherein when the dynamically received data items are updated, at least one connection is identified as a result thereof via the processor.

18. A method for identifying connections between data items in an updatable data repository, the method comprising:

dynamically receiving a plurality of data items from the updatable data repository, the plurality of data items being provided by a plurality of updatable sources, each data item including one or more controlled terms;

determining one or more topics based on the one or more controlled terms, each topic comprising a specific combination of controlled terms using unsupervised machine learning and non-negative matrix factorization;

displaying the dynamically received data items on a display of a display device;

receiving a selection of a topic of the one or more topics on a user interface on the display;

defining degrees of similarity between the plurality of data items;

ranking the plurality of data items with respect to one another based on the degree of similarity therebetween; and identifying one or more connections between two or more data items of the plurality of data items from different updatable sources based on the two or more data items being associated with the selection of the topic of the one or more determined topics and based on the ranking between the two or more data items;

wherein the plurality of data items are updated contemporaneously when the sources thereof are updated.

19. The method of claim 18, wherein, for each data item, each controlled term defines one or more characteristics of the data item.

20. The method of claim 18, wherein the plurality of data items only comprise controlled terms.

21. The method of claim 18, wherein the degree of similarity between two data items is defined by at least one of a number and a frequency of controlled terms shared by the two data items.

22. The method of claim 18, wherein for each given data item, other data items are individually ranked based on the degree of similarity between the given data item and each of the other data items.

23. The method of claim 18, wherein any two data items share a same rank.

24. The method of claim 18, further comprising:

defining a rank threshold;

wherein identifying the one or more connections comprises identifying data items that share a rank that is higher than the rank threshold.

25. The method of claim 18, further comprising providing the one or more identified connections.

* * * * *